US005554098A

United States Patent [19]
Yabe et al.

[11] Patent Number: 5,554,098
[45] Date of Patent: Sep. 10, 1996

[54] ENDOSCOPE SYSTEM INCLUDING ENDOSCOPE AND DISPOSABLE PROTECTION COVER

[75] Inventors: Hisao Yabe, Hachioji; Yoshihiro Iida, Tama; Akira Suzuki; Hideo Ito, both of Hachioji; Yoshio Tashiro, Hino; Minoru Yamazaki, Hachioji; Osamu Tamada, Hachioji; Keiichi Arai, Hachioji, all of Japan

[73] Assignee: Olympus Optical Co., Ltd., Tokyo, Japan

[21] Appl. No.: 38,720

[22] Filed: Mar. 29, 1993

[30] Foreign Application Priority Data

| Feb. 26, 1993 | [JP] | Japan | 5-007454 U |
| Feb. 26, 1993 | [JP] | Japan | 5-038144 |
| Mar. 1, 1993 | [JP] | Japan | 5-040013 |
| Mar. 3, 1993 | [JP] | Japan | 5-008551 U |

[51] Int. Cl.⁶ .......................................... A61B 1/00
[52] U.S. Cl. .................... 600/121; 600/122; 600/123; 600/124
[58] Field of Search ........................ 128/4, 6, 844, 128/917, 918, 919; 359/510; 600/121, 122, 123, 124

[56] References Cited

U.S. PATENT DOCUMENTS

| 3,035,691 | 5/1962 | Rasmussen et al. . |
| 3,633,758 | 1/1972 | Morse . |
| 4,366,901 | 1/1983 | Short . |
| 4,646,722 | 3/1987 | Silverstein et al. . |
| 4,715,360 | 12/1987 | Akui et al. . |
| 4,721,097 | 1/1988 | D'Amelio . |
| 4,741,326 | 5/1988 | Sidall et al. . |
| 4,779,727 | 10/1988 | Taterka et al. . |
| 4,825,850 | 5/1989 | Opie et al. . |
| 4,858,001 | 8/1989 | Milbank et al. . |
| 4,869,238 | 9/1989 | Opie et al. . |
| 4,877,033 | 10/1989 | Seitz . |
| 4,878,485 | 11/1989 | Adair . |
| 4,947,827 | 8/1990 | Opie et al. . |
| 4,991,564 | 2/1991 | Takahashi et al. . |
| 4,991,565 | 2/1991 | Takahashi et al. . |
| 5,025,778 | 6/1991 | Silverstein et al. ................. 128/4 |
| 5,050,585 | 9/1991 | Takahashi . |
| 5,082,112 | 1/1992 | Dunklee . |
| 5,105,942 | 4/1992 | van Veen et al. . |
| 5,131,537 | 7/1992 | Gonzales . |
| 5,198,894 | 3/1993 | Hicks . |
| 5,201,908 | 4/1993 | Jones ................................. 128/4 |
| 5,217,001 | 6/1993 | Nakao et al. ...................... 128/4 |
| 5,237,984 | 8/1993 | Williams, III et al. . |
| 5,301,657 | 4/1994 | Lafferty et al. . |

FOREIGN PATENT DOCUMENTS

| 0341719A1 | 11/1989 | European Pat. Off. . |
| 0349479A1 | 1/1990 | European Pat. Off. . |
| 325138 | 11/1992 | Japan ................................. 128/4 |

*Primary Examiner*—Richard J. Apley
*Assistant Examiner*—Beverly M. Flanagan
*Attorney, Agent, or Firm*—Watson Cole Stevens Davis, P.L.L.C.

[57] ABSTRACT

In an endoscope system including an endoscope having an insertion section insertable into a cavity under inspection and an operation section having at least one operation switch, said operation section being connected to a proximal end of said insertion section and a disposable protection cover having an insertion section cover for covering said insertion section of the endoscope and an operation section cover for covering said operation section of the endoscope, said insertion section cover includes a forceps channel through which existing forceps for use in ordinary without-cover endoscopes can be inserted. An inner diameter of the forceps channel is determined to be slightly larger than an outer diameter of most frequently used forceps or standard forceps whose number shows a peak in the outer diameter series of the forceps.

12 Claims, 25 Drawing Sheets

FIG_1
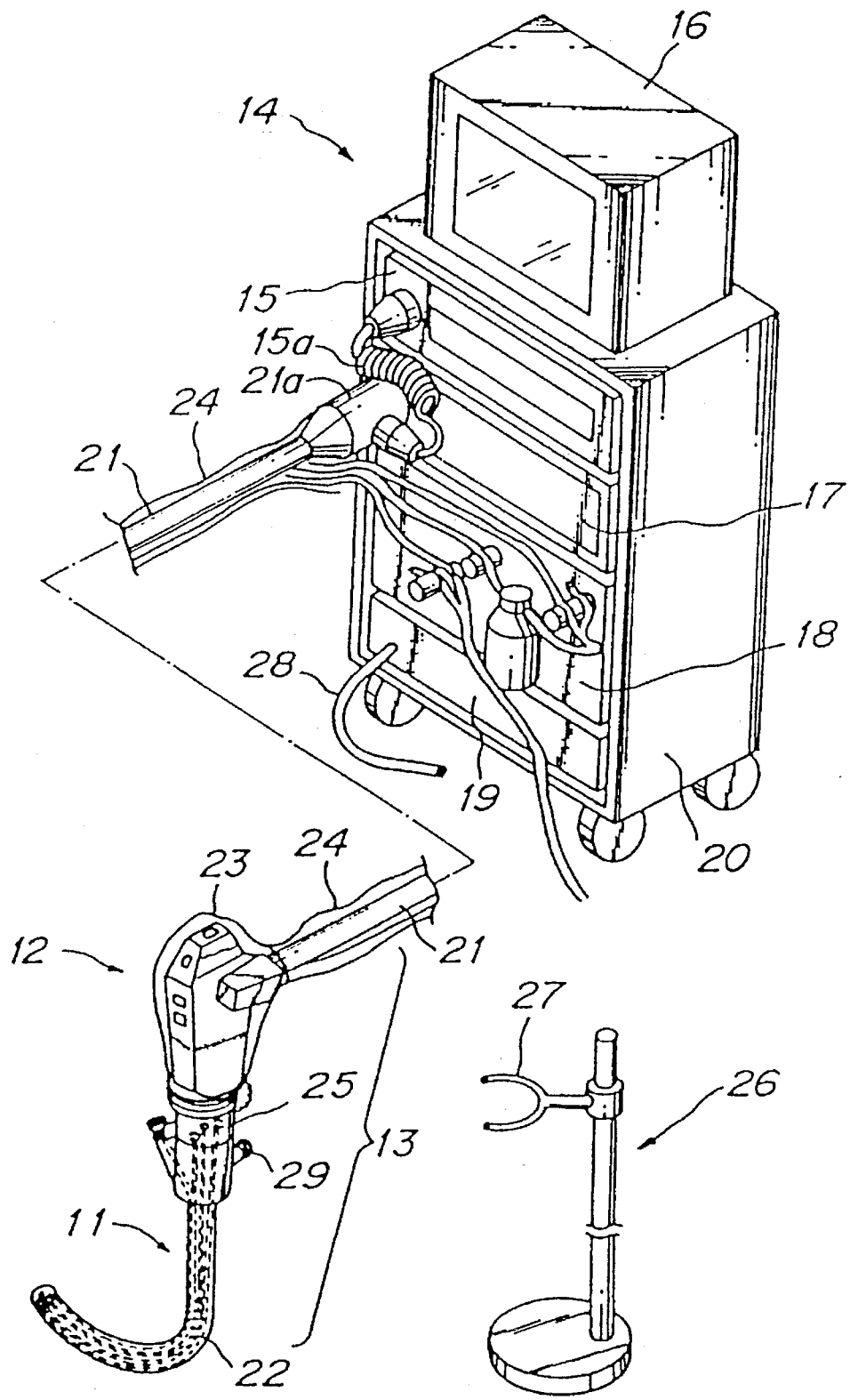

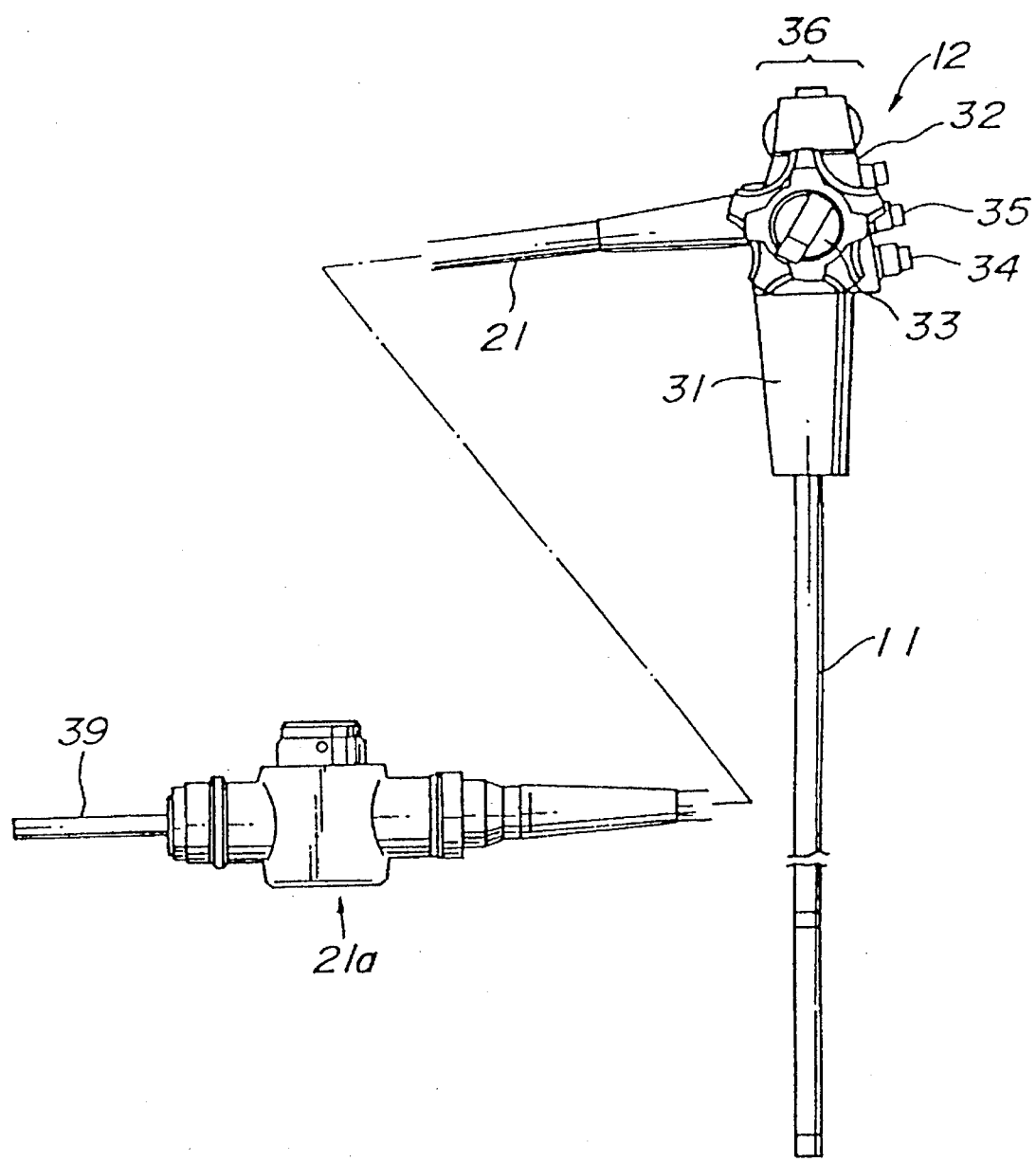

FIG_3
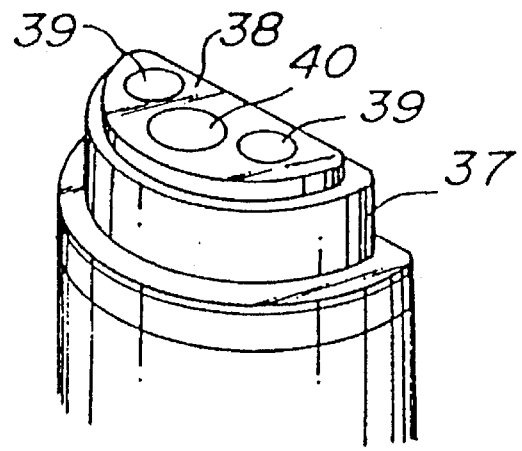
FIG_4
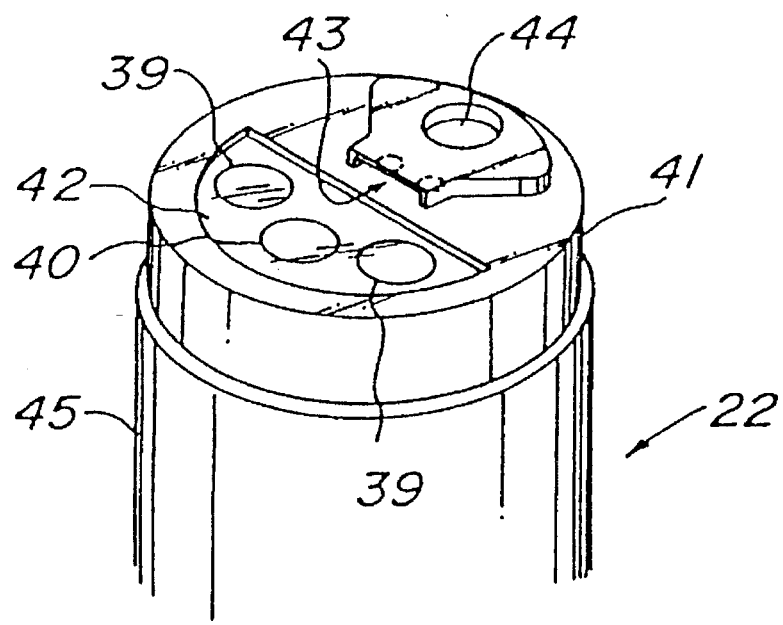

FIG_6
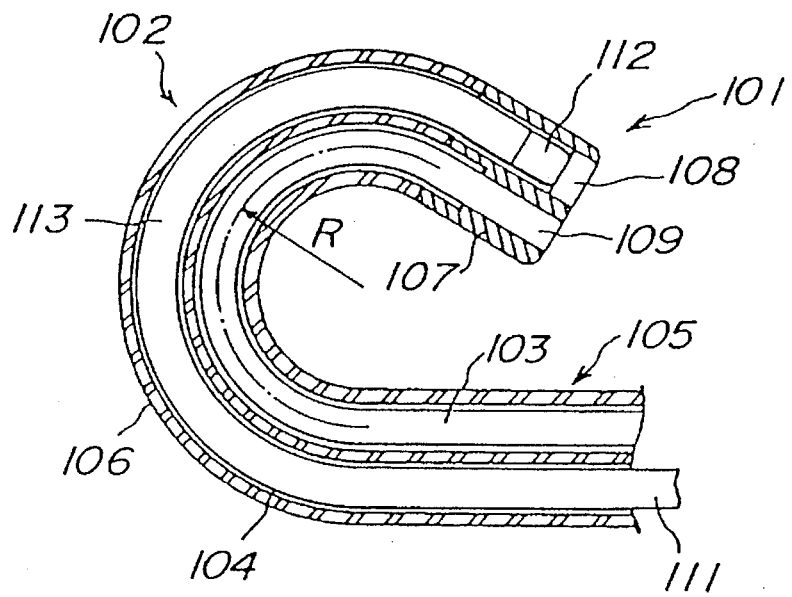
FIG_7
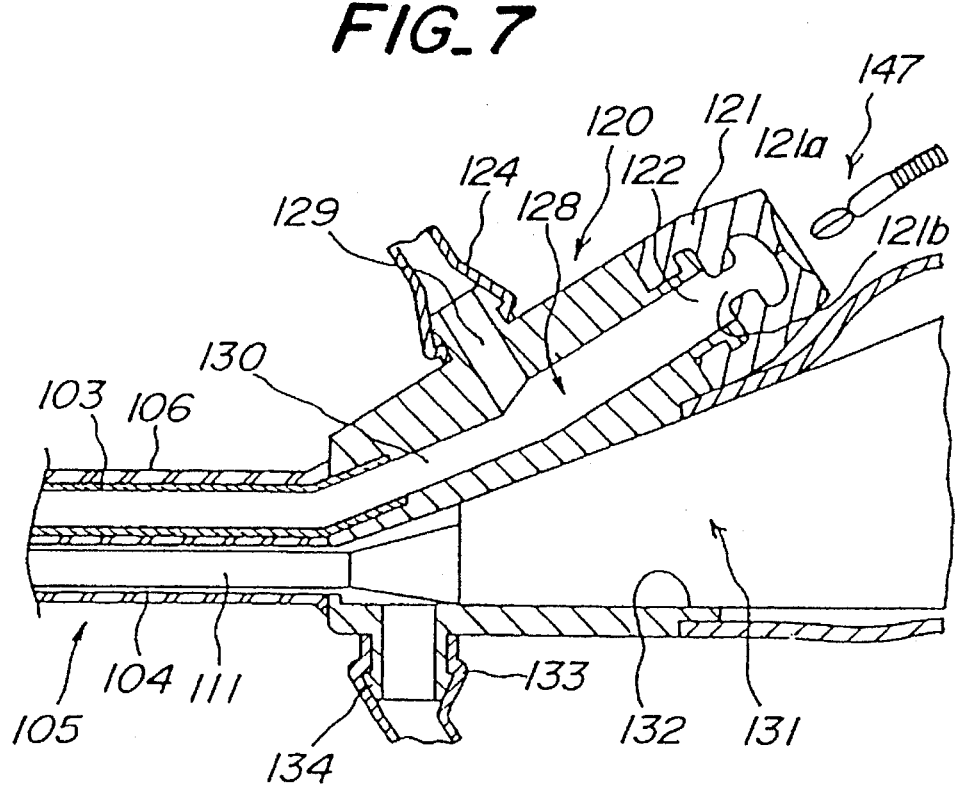

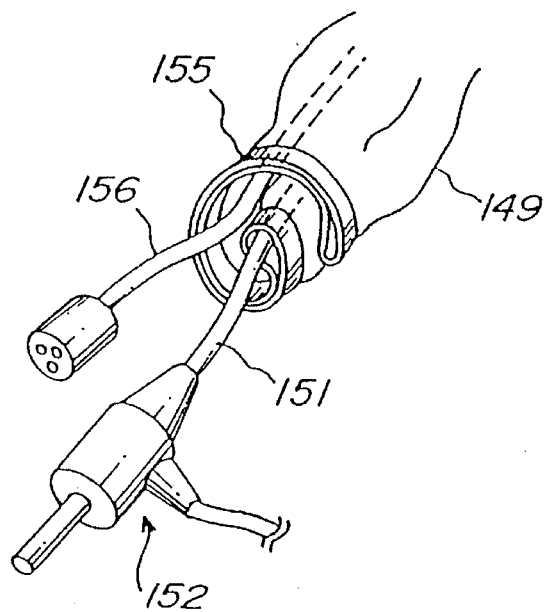
FIG_11
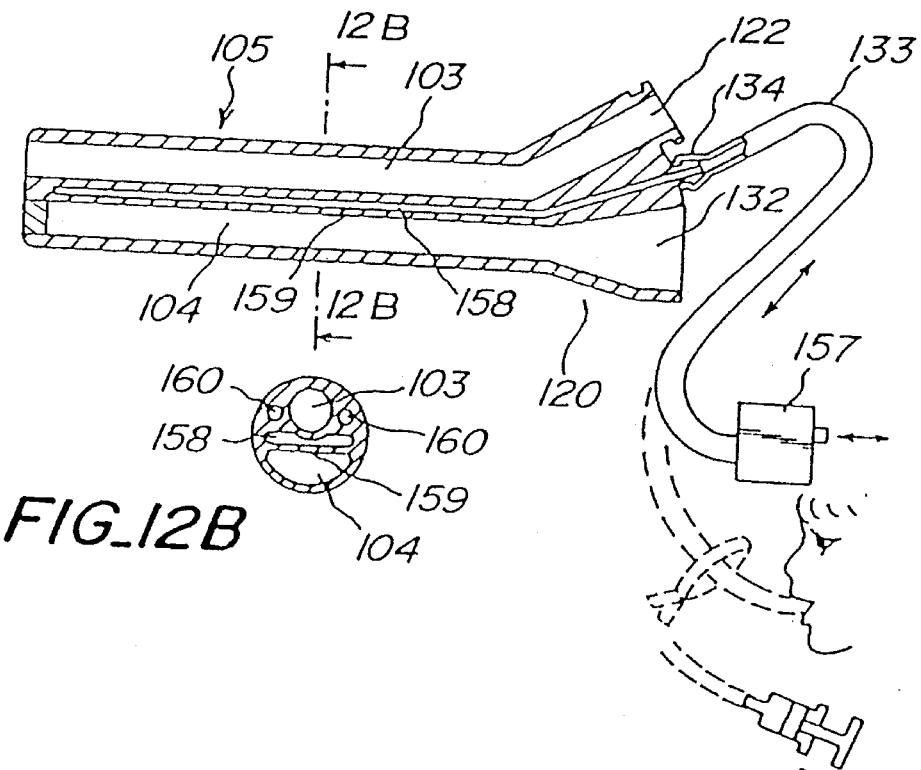
FIG_12A
FIG_12B

FIG_13
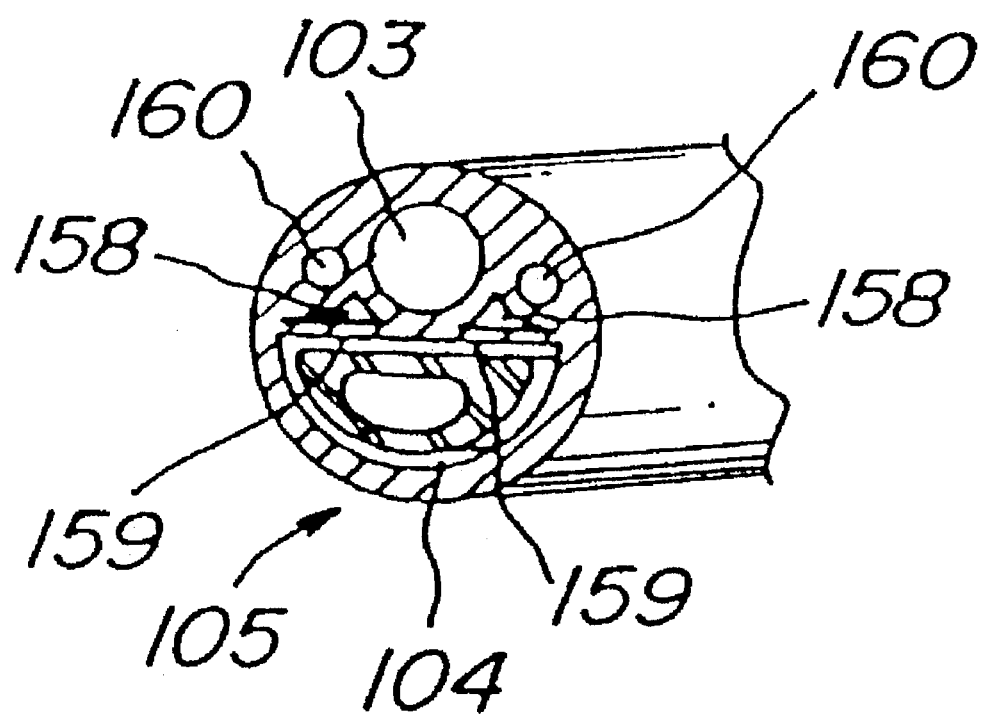

FIG. 14

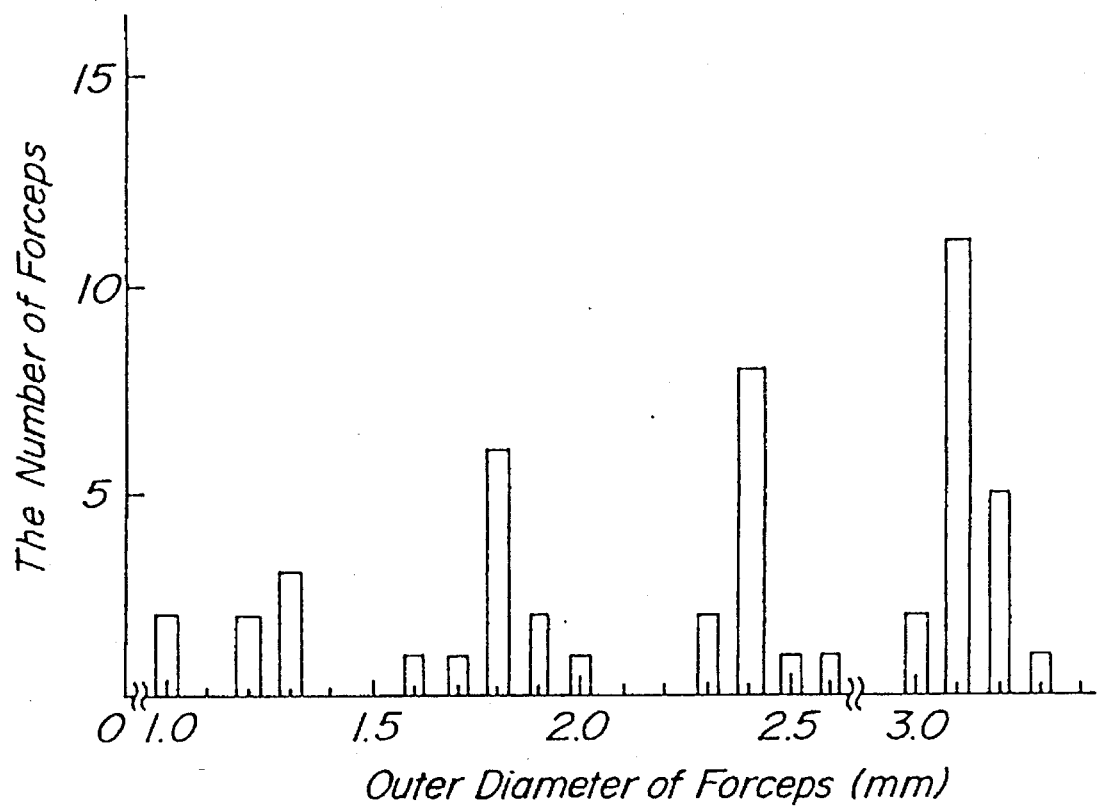
FIG_15

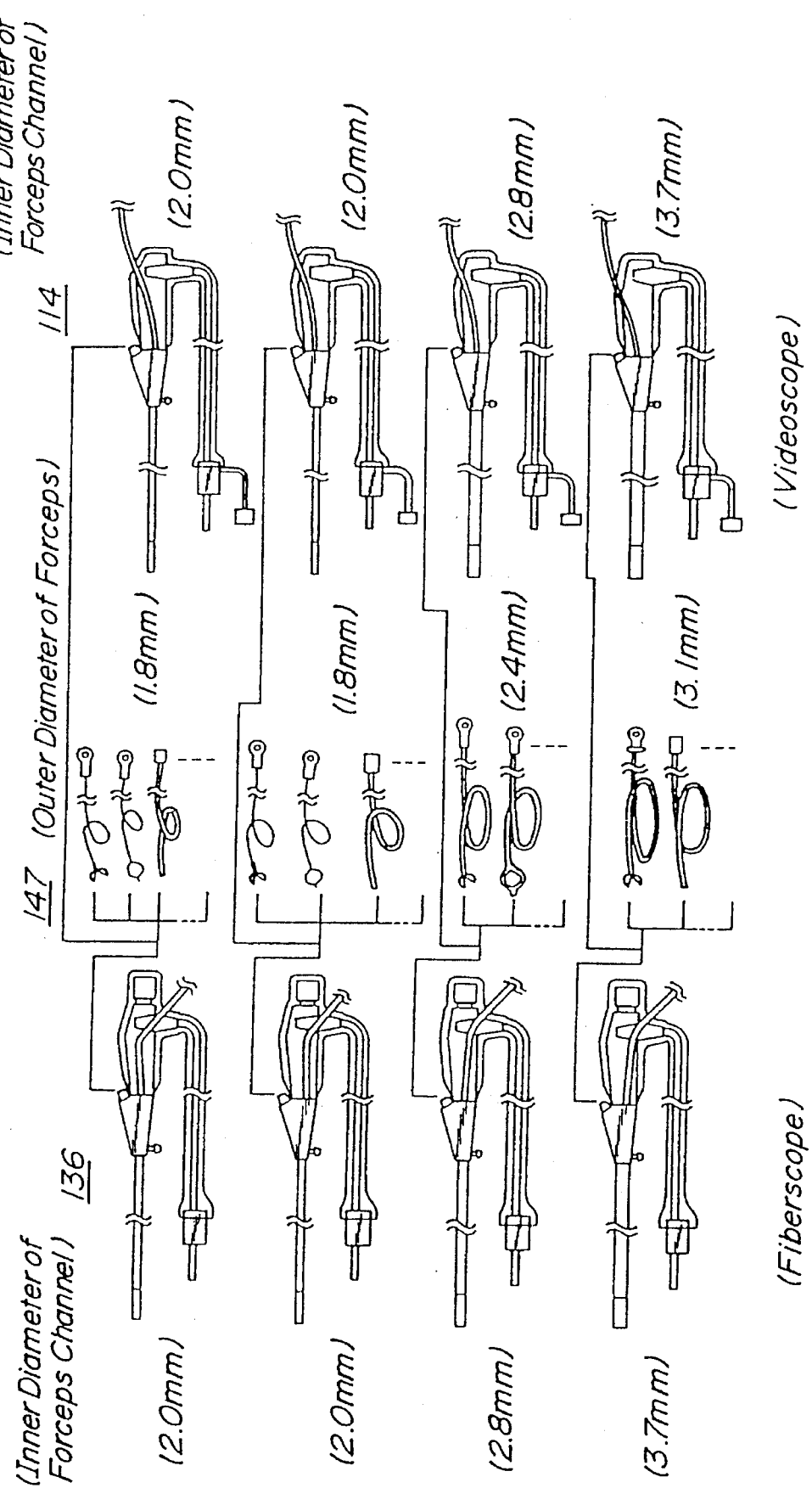
FIG_16

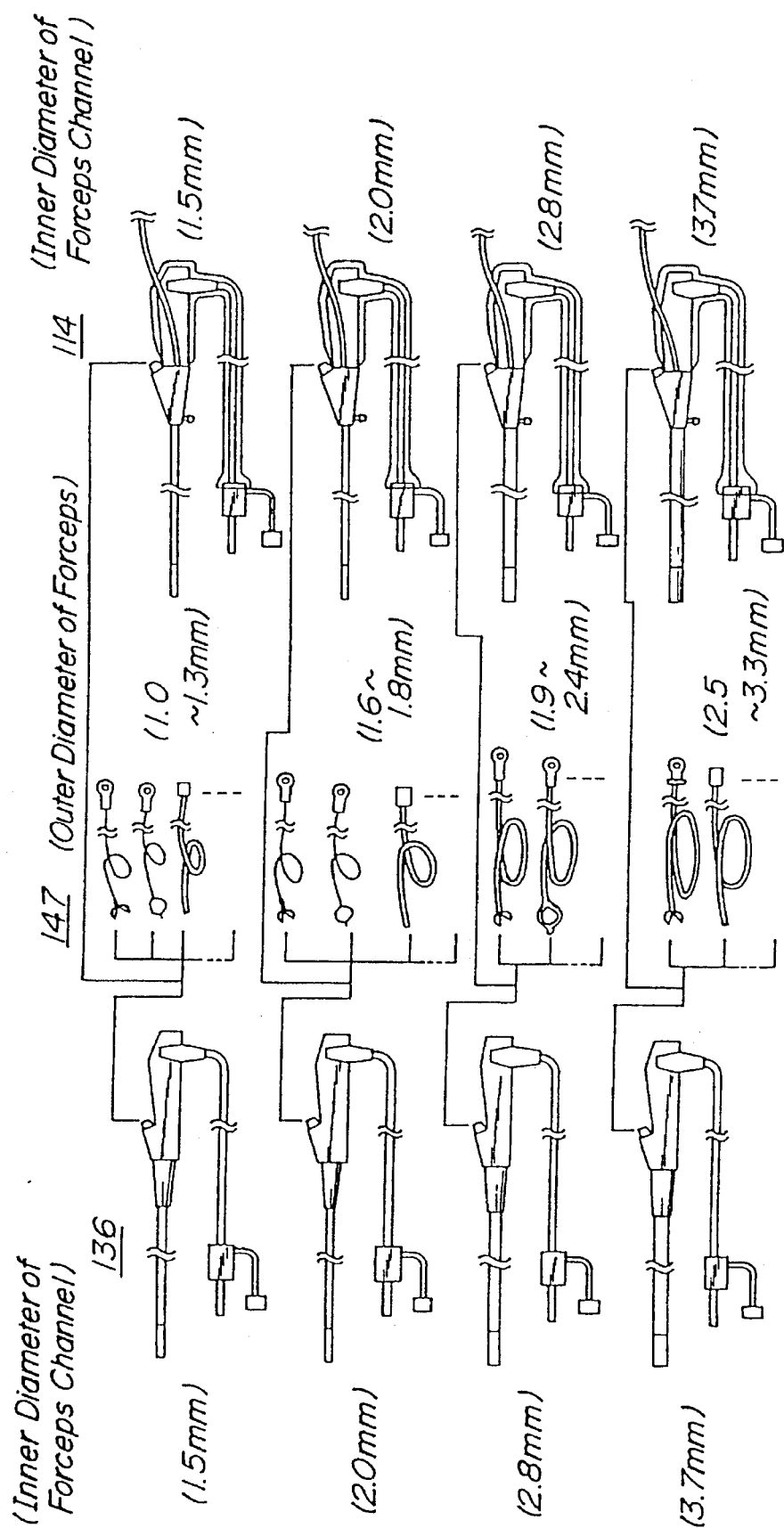
FIG_17

FIG_18A
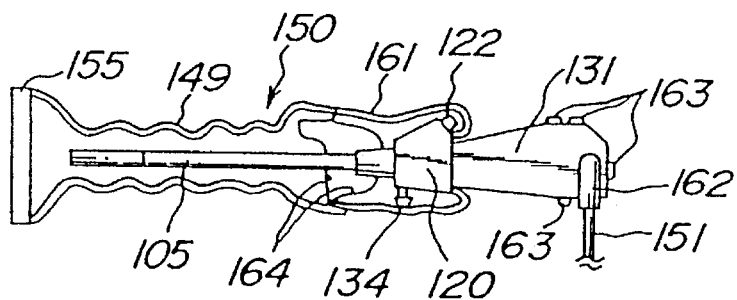
FIG_18B
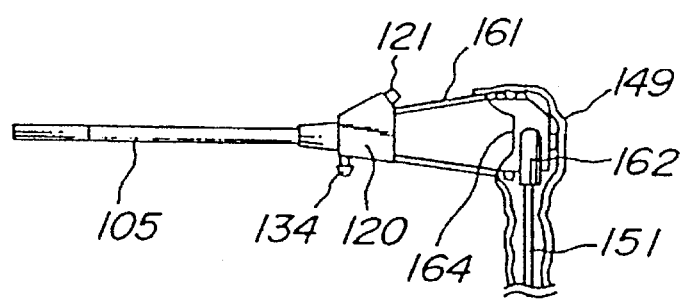
FIG_19A
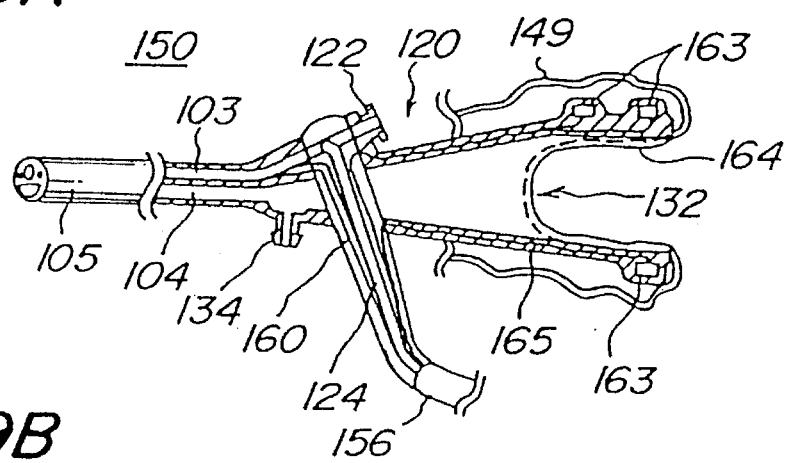
FIG_19B
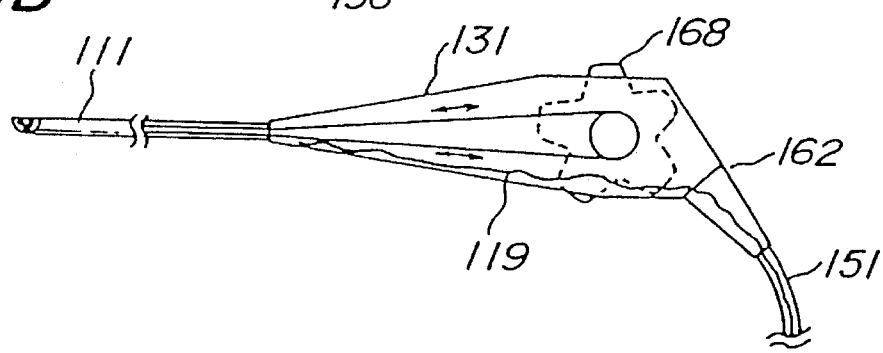

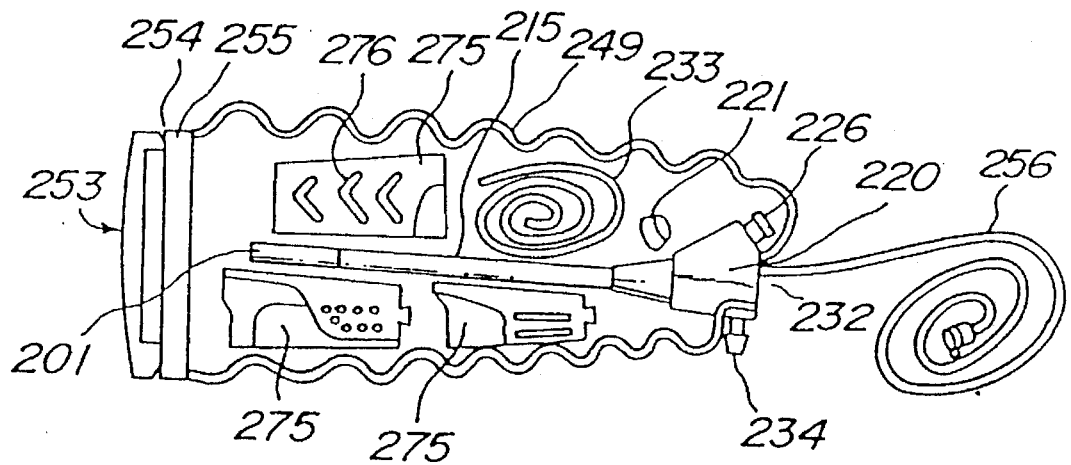
FIG_21
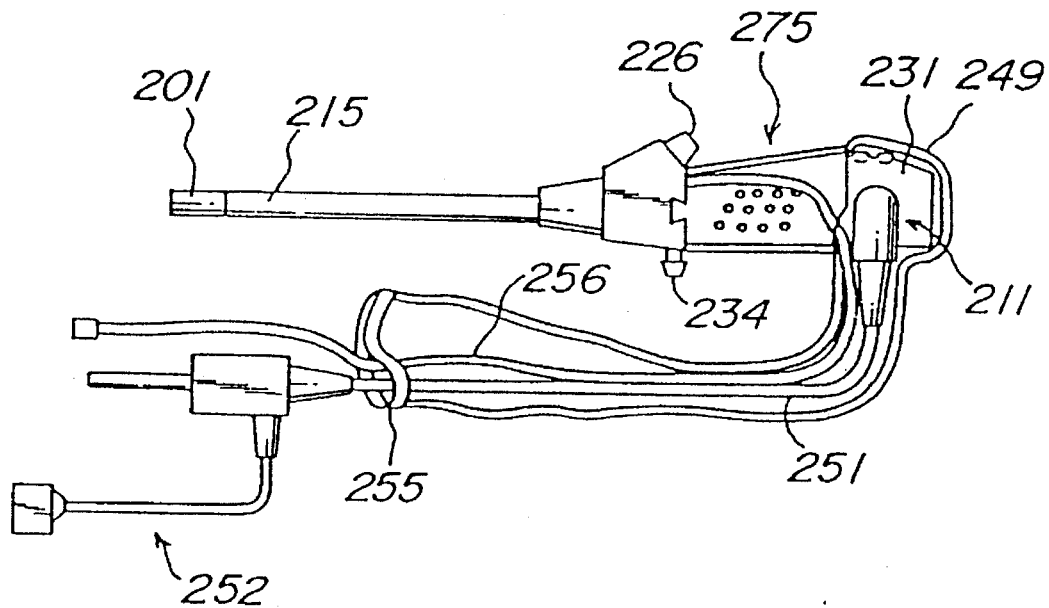
FIG_22

FIG_23
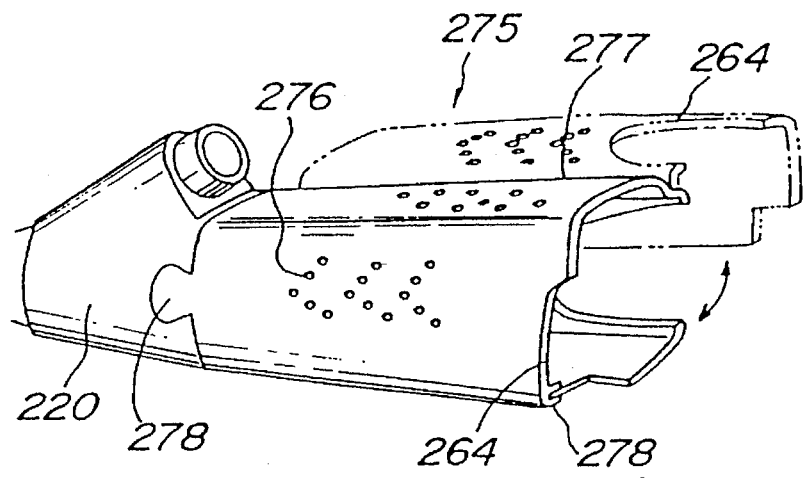
FIG_24
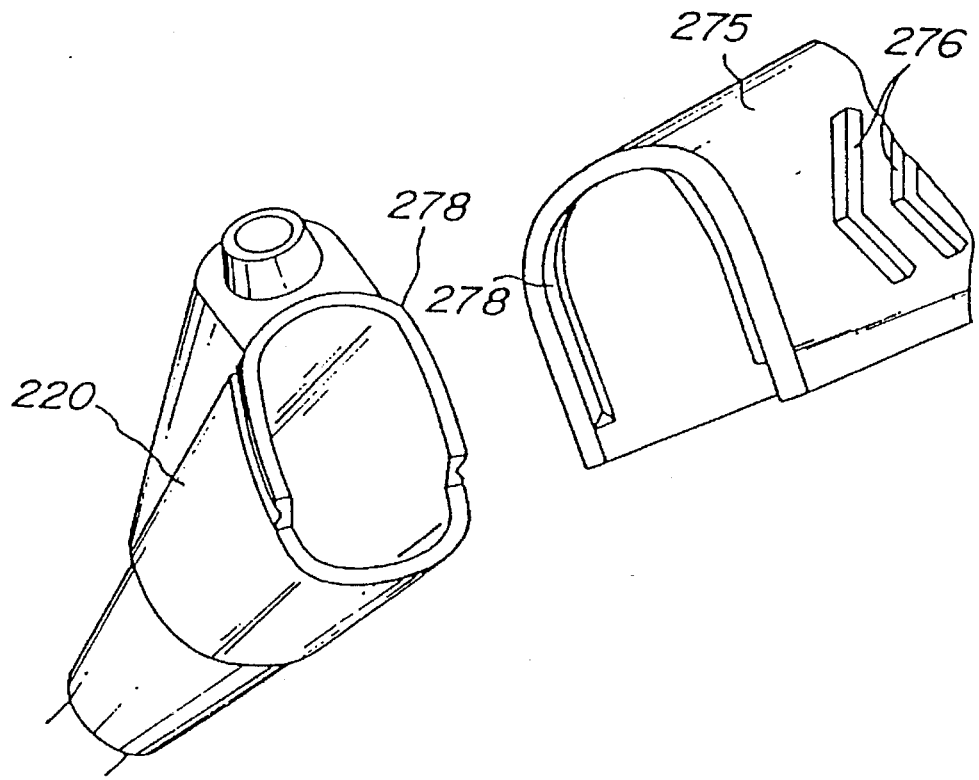

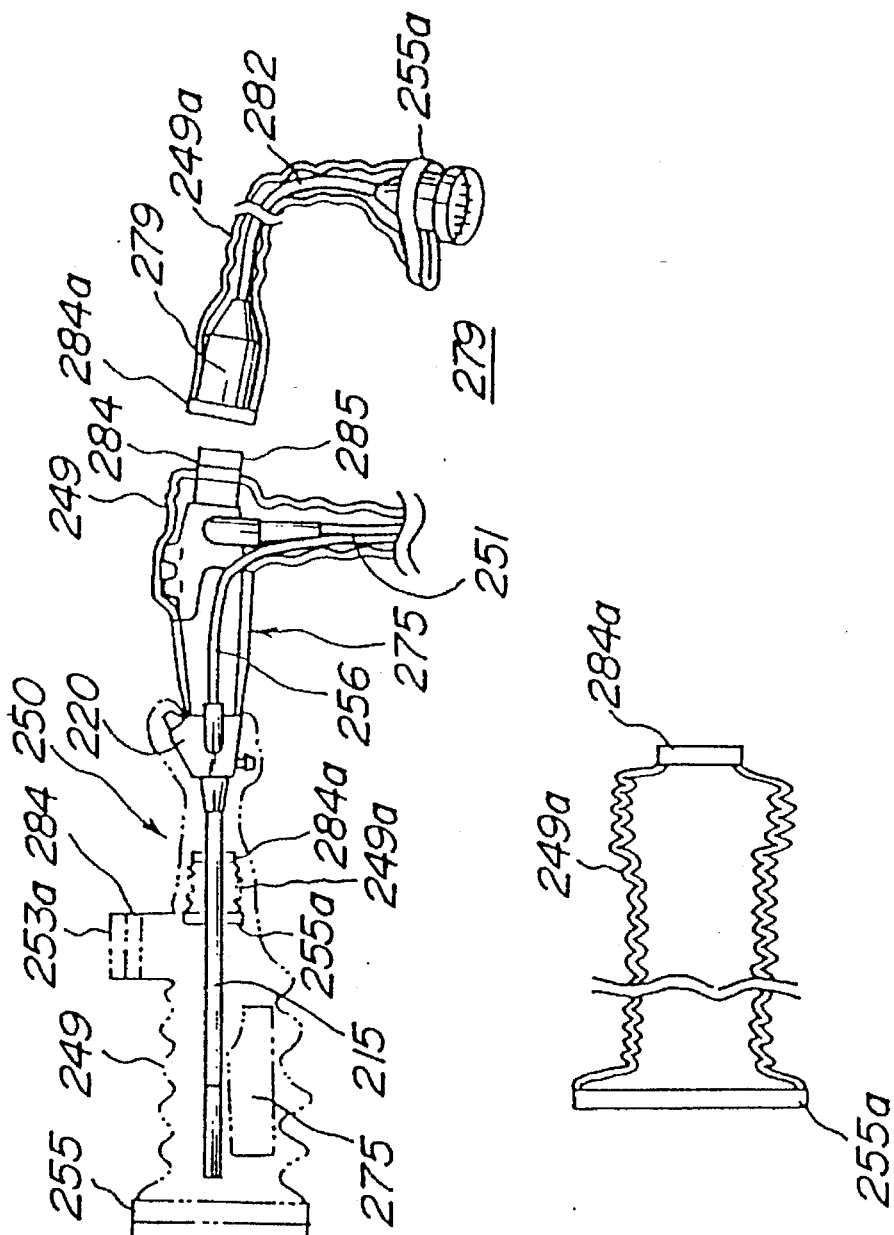

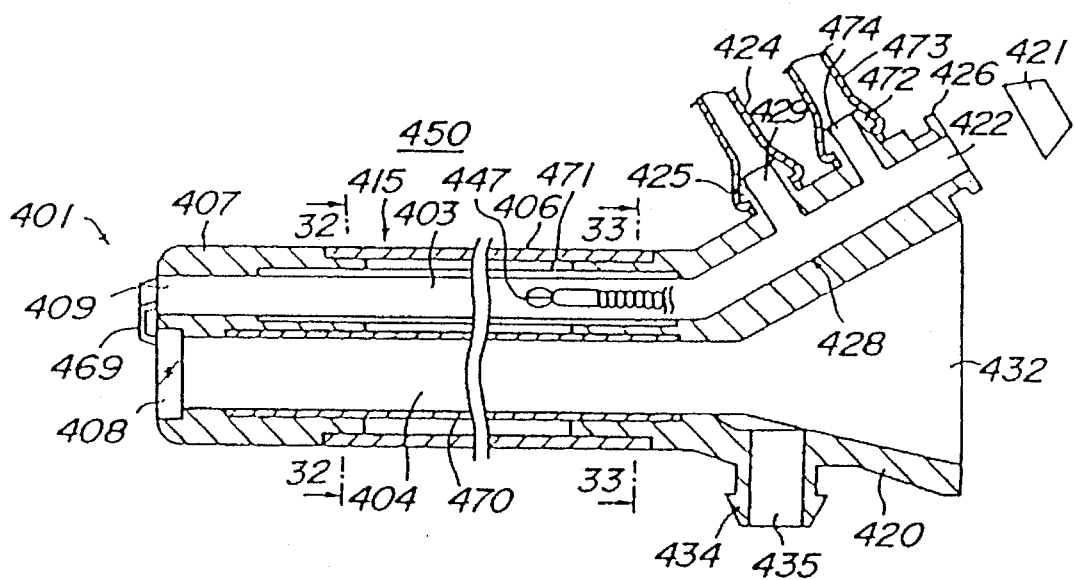
FIG_30

FIG_31
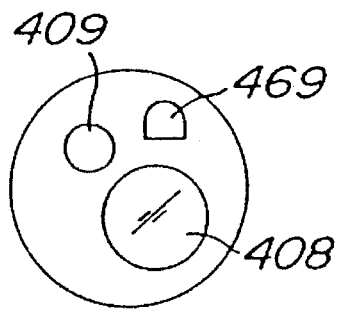
FIG_32
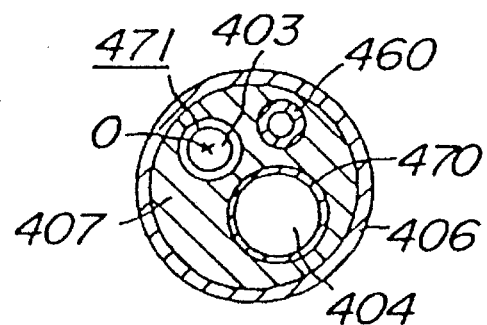
FIG_33
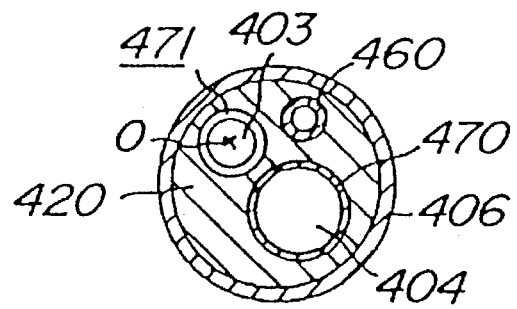

FIG_34A
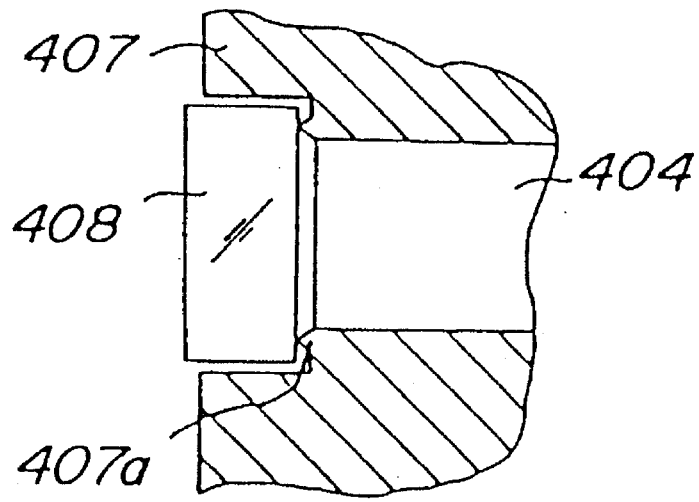
FIG_34B
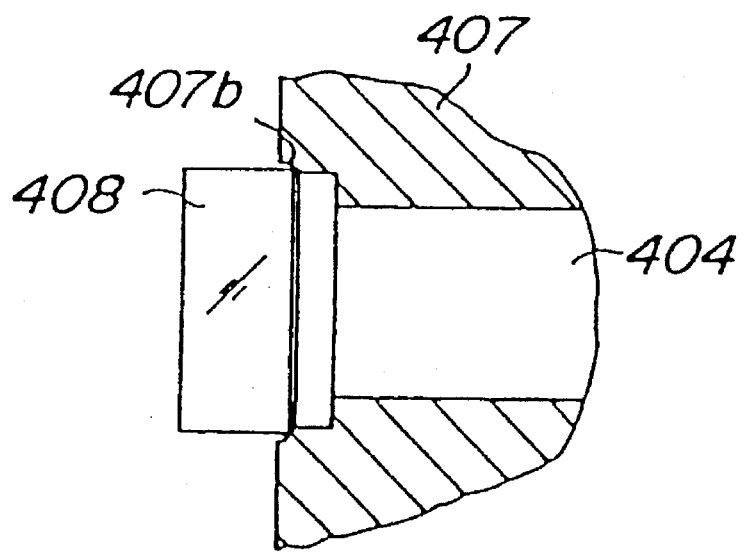

FIG_35A
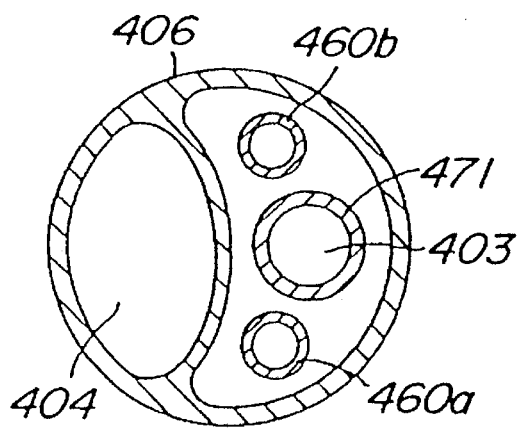
FIG_35B
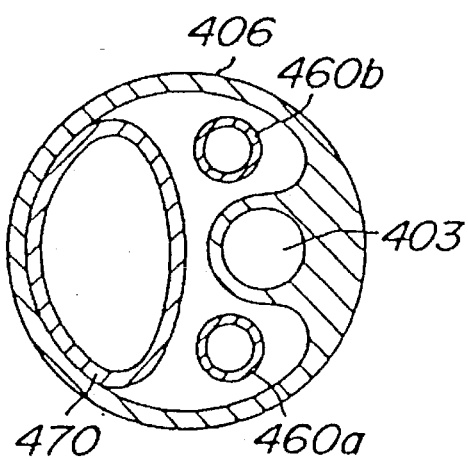
FIG_35C
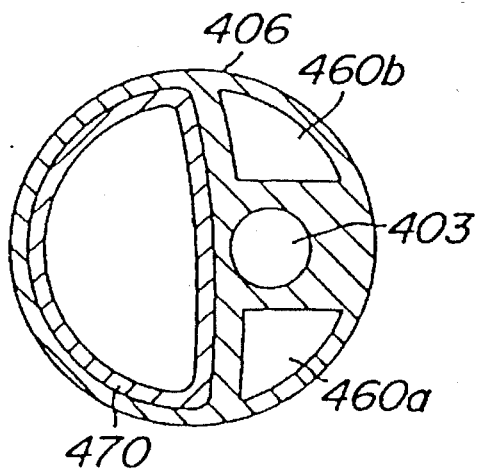
FIG_35D
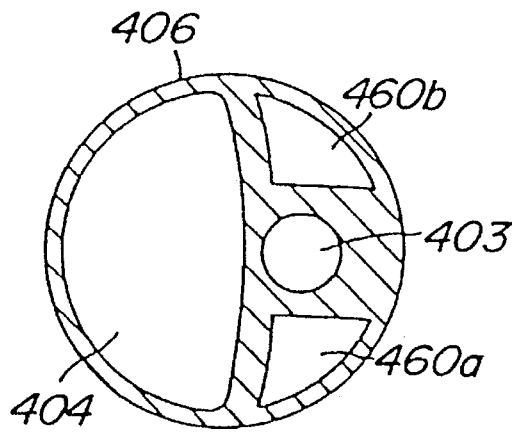

ENDOSCOPE SYSTEM INCLUDING ENDOSCOPE AND DISPOSABLE PROTECTION COVER

BACKGROUND OF THE INVENTION

1. Field of the Invention

The present invention relates to an endoscope system including an endoscope having an insertion section which is insertable into a cavity under inspection and an operation section to which a proximal end of the insertion section is connected, and a disposable protection cover having an insertion section cover for covering the insertion section of the endoscope and an operation section cover for covering the operation section of the endoscope.

2. Related Art Statements

An endoscope system has been widely utilized for providing diagnostic and therapeutic indications for coeliac cavities of patients and for internal inspection of mechanical structures. To this end, various kinds of endoscopes have been developed. For instance, in order to inspect or treat the oesophagus, stomach and duodenum, upper endoscopes have been utilized. Further, colonoscopes have been developed to examine colons, and sigmoidoscopes have been proposed to inspect rectums and sigmoid colons. When the endoscope is used, an insertion portion of the endoscope has to be inserted into a cavity of a patient, so that the outer surface of the insertion section of the endoscope is contaminated with living tissues and liquids. Such a contaminated endoscope could not be successively used for other patients. Therefore, once the endoscope is used to diagnose and/or treat a patient, it is necessary to clean and sterilize the endoscope. Of course, the cleaning of the endoscope requires a substantial amount of time and during this cleaning time, it is impossible to perform the endoscopic procedure by using this endoscope. In order to mitigate such idle time, it is necessary to prepare a large number of endoscopes. However, endoscopes are rather expensive, so that it is practically difficult to prepare a large number of endoscopes, particularly in a small hospital or clinic. Therefore, in almost all hospitals and clinics, in practice, after the endoscope has been used for examining or treating a patient, the endoscope is immediately cleaned. Typically, this cleaning requires several minutes (up to ten minutes). In order to effect complete washing and sterilization, the cleaning has to be performed for several tens of minutes.

Further, the endoscope has various channels such as an air channel, a water channel, a suction channel, and a forceps channel which extend along the insertion section from a proximal end to a distal end thereof, and these channels, except for the forceps channel, are connected via tubes to respective devices such as an air supply pump, a water supply pump, a water suction pump and an air suction pump. These channels are subjected to contact with living tissues and liquids. However, in order to clean these channels of the endoscope completely, a relatively long period of time is required. Thus, the endoscope can not be utilized efficiently during the long cleaning time. In a large hospital or clinic, a large number of endoscopes may be prepared in order to mitigate the problem of cleaning time. However, this solution results in an increase in operating costs. Further, in small clinics, it is practically impossible to prepare a number of expensive endoscopes.

Moreover, the endoscope might be broken during cleaning, and the usable life of the endoscope is liable to be shortened by the cleaning.

In order to avoid the above-explained various problems, there has been proposed an endoscope system, in which the endoscope is covered with a disposable protection sheath-like cover having channels formed therein. For instance, U.S. Pat. Nos. 4,721,097, 4,741,326, 4,825,850, 4,869,238, 4,991,564, 4,991,565 and 5,050,585 disclose various kinds of disposable protection sheath-like covers having channels formed therein. In U.S. Pat. No. 4,646,722, there is shown an endoscope system in which the endoscope is covered with a protection sheath, while a tube having channels formed therein is inserted into a U-shaped cutout formed in an outer surface of the endoscope along a longitudinal axis thereof. Upon diagnosis, the insertion section of the endoscope is covered with the protection sheath, and after the inspection, the sheath is removed from the insertion section and is then discarded. Therefore, it is no longer necessary to clean the endoscope after every inspection.

In the above-mentioned U.S. Patents, the protection sheath-like cover is constructed to cover only the insertion section of the endoscope, but does not cover an operation section of the endoscope. It should be noted that the operation section of the endoscope is handled by doctors and operators and thus is brought into contact with the living tissues and liquids of a patient. Therefore, in order to remove the contamination of the operation section of the endoscope due to such living tissues and liquids, it is advantageous to cover not only the insertion section, but also the operation section of the endoscope. In European Patent Publication No. 0 349 479 A1, there is disclosed an endoscope system, in which not only the insertion section, but also the operation section, of the endoscope are covered with a disposable protection cover. That is to say, the protection cover comprises a sheath-like portion for covering the insertion section of the endoscope and a bag-like portion for covering the operation section, the sheath-like portion and bag-like portion being integrally formed. It has been also proposed to form the sheath-like portion and bag-like portion as separate covers. For instance, in European Patent Publication No. 0 341 719 A1, there is proposed another known endoscope system, in which an insertion section of an endoscope is covered with a sheath-like disposable protection cover and an operation section of the endoscope is covered with a bag-like disposable protection cover which is mated or joined with the sheath-like cover in order to prevent contamination through the junction of the sheath-like cover and the bag-like cover.

In the known endoscope system including the insertion section cover having an insertion section inserting channel and a forceps channel, the construction of the forceps channel, e.g. length, inner diameter, strength, material, configuration and shape, is not formed such that various forceps, i.e. treating tools for ordinary without-cover (coverless) endoscopes, which are not used together with the disposable protection covers, can be commonly used for the endoscope system. That is to say, specially prepared forceps are provided for use in the endoscope system. As is apparent, this is very inconvenient and is not economical. Further, if a forceps for a coverless endoscope is erroneously used for the endoscope system including the endoscope and disposable protection cover, either or both of the forceps and the protection cover might be broken.

Further, in the known endoscope system, various kinds of forceps are prepared and a desired forceps is used. In the present specification, two forceps for performing the same treatment, but having different outer diameters, are considered to belong to different kinds of forceps. It should be noted that the outer diameter means a maximum diameter of a forceps and generally a diameter of a distal end treating portion. As stated above, there have been proposed various kinds of forceps for use in the ordinary coverless endoscopes, and these forceps can be classified into several groups in accordance with the outer diameter. Similarly, various kinds of forceps for use with disposable protection covers of the above-mentioned endoscope system can be classified into several groups in accordance with the outer diameters. However, the forceps groups for the disposable protection covers are not mated with the forceps groups for the coverless endoscopes. This means that the forceps for the coverless endoscopes can not be commonly used for the disposable protection covers, and thus sometimes suitable treatments can not performed. Moreover, an operator can not utilize the familiar forceps for the coverless endoscopes, so that the operator might be subjected to mental stress.

For coverless endoscopes, there have been prepared a very large number of different kinds of forceps, and thus the number of groups of forceps is quite large. However, in the endoscope system including the disposable protection cover with a forceps channel and the endoscope without a forceps channel, it is desired to discard the forceps together with the cover. Therefore, it is desired to prepare forceps which are classified into a smaller number of groups.

In the above-mentioned endoscope system including the endoscope and disposable protection cover with forceps channel, a position of the forceps channel in a cross-section, at the distal end of the insertion section cover, is not identical with a position of the forceps channel in a cross-section at a connecting portion between the insertion section cover and the operation section cover. In other words, the forceps channel is twisted within the insertion section cover. Thus, the forceps can not be smoothly inserted into the forceps channel, and a relatively large force is required for inserting the forceps. Furthermore, during the insertion of the forceps, a tip of the forceps might be hit on an inner wall of the forceps channel and might be broken or the inner wall damaged. The above-mentioned drawback is manifest when a length of the forceps is long. When the forceps channel is twisted, the forceps channel is clogged upon bending the protection cover, and therefore the forceps could not be inserted any more.

In the known disposable protection cover, the operation section cover for covering the operation section of the endoscope is made of soft material, because the operating members provided on the operation section have to be operated on the protection cover. That is to say, if the operation section cover is made of rigid or semi-rigid material, the operating members could not be operated positively. Therefore, the operation section cover might move relative to the operation section of the endoscope. This results in that the operator can not grasp the operation section firmly, and therefore the operator can not handle the operation section effectively and might be subject to fatigue.

SUMMARY OF THE INVENTION

The present invention has for its object to provide a novel and useful endoscope system in which the forceps for use in coverless endoscopes can be commonly utilized for the endoscope system having the disposable protection cover with forceps channel, so that the above-explained erroneous selection of the forceps can be positively prevented and the examination procedure can be performed easily and reliably.

It is another object of the invention to provide a novel and useful endoscope system, in which various kinds of forceps can be efficiently utilized.

It is another object of the invention to provide a novel and useful disposable protection cover with a forceps channel, in which the forceps can be smoothly inserted into the forceps channel without damaging the forceps or an inner wall of the forceps channel.

It is still another object of the invention to provide a novel and useful disposable protection cover, in which the operation section of the endoscope covered with the protection cover can be firmly grasped, so that the operator can handle the operation section easily and positively without feeling fatigued.

According to a first aspect of the present invention, an endoscope system includes an insertion section insertable into a cavity under inspection and an operation section to which a proximal end of the insertion section is connected and a disposable protection cover for covering at least the insertion section of the endoscope and having a forceps channel extended within the protection cover, wherein the forceps channel of the disposable protection covers is constructed such that forceps for use in normal coverless endoscopes can be used for the disposable protection cover.

According to the invention, a length and an inner diameter of the forceps channel of the disposable protection cover are set on the basis of the forceps to be used such that several types of protection covers having different lengths and inner diameters of forceps channels are prepared in accordance with organs to be treated and treatment methods. Further, the configuration and shape of the forceps channel are determined such that forceps for a normal coverless endoscope can be inserted into the forceps channel. In this case, forceps having a moving mechanism at a distal end, such as grasping forceps, can be inserted and removed into and from the forceps channel. Further, when the insertion section is bent by a maximum angle, the forceps can be inserted and removed into and from the forceps channel. In this connection, it should be noted that the inner diameter of the forceps channel should not be made larger unnecessarily, because then a diameter of the disposable protection cover also becomes larger.

Moreover, according to the invention, contaminated liquids should not flow out of the forceps inlet opening during the examination or during the sucking operation and should not be spread when the forceps is removed from the forceps channel. Further, the forceps may be of a disposable type or of a reusable type.

According to a second aspect of the invention, an endoscope system includes at least one endoscope having an insertion section insertable into a cavity under inspection and an operation section to which a proximal end of the insertion section is connected, a plurality of disposable protection covers, each having an insertion section cover for covering an insertion section of an endoscope and a forceps channel extending within the insertion section cover, inner diameters of the forceps channels being different from each other, and a plurality of forceps having different outer diameters, wherein each of the inner diameters of the forceps channels of the plurality of disposable protection covers is set to be larger, by a predetermined amount, than the substantially same outer diameter of a plurality of forceps, the number of which is maximized in an outer diameter series.

In a preferable embodiment of the endoscope system according to the invention, there are prepared three kinds of disposable protection covers with forceps channels having inner diameters of 2.0 mm, 2.8 mm and 3.7 mm. Then, for the protection cover having a forceps channel of 2.0 mm, a plurality of forceps having outer diameters smaller than 1.8 mm can be utilized, for the protection cover having a forceps channel of 2.8 mm, a plurality of forceps having outer diameters smaller than 2.4 mm can be used, and for the protection cover with the forceps channel having a diameter of 3.7 mm, a plurality of forceps having outer diameters smaller than 3.1 mm can be utilized. According to the invention, the predetermined amount should be determined such that the forceps can be easily inserted into the forceps channel, the forceps can be operated effectively, and liquids can be effectively sucked through the forceps channel even if the forceps is inserted therein.

According to a third aspect of the invention, a disposable protection cover is provided for use in an endoscope system including an endoscope having an insertion section insertable into a cavity under inspection and an operation section to which a proximal end of the insertion section is connected and a disposable protection cover having an insertion section cover for covering the insertion section of the endoscope, an operation section cover for covering the operation section of the endoscope and a forceps channel extending from a proximal end to a distal end of the insertion section cover. A center coordinate of the forceps channel in a cross-section perpendicular to a longitudinal axis of the insertion section cover at the distal end of the insertion section cover is substantially identical with a center coordinate of the forceps channel in a cross-section perpendicular to the longitudinal axis at a connecting portion between the insertion section cover and the operation section cover.

In such a disposable protection cover according to the invention, the forceps channel extends straight within the insertion section cover, and thus the forceps can be easily inserted into the forceps channel without causing any trouble.

According to a fourth aspect of the invention, a disposable protection cover is provided for use in an endoscope system including an endoscope having an insertion section insertable into a cavity under inspection and an operation section to which a proximal end of the insertion section is connected and a disposable protection cover having an insertion section cover for covering the insertion section of the endoscope and an operation section cover for covering the operation section of the endoscope. The operation section cover comprises a first cover portion, for covering a grip portion of the operation section, made of rigid or semi-rigid material and a second cover portion, for covering the remaining portion of the operation section of the endoscope, made of soft material.

In such a disposable protection cover according to the invention, the grip portion of the operation section of the endoscope is covered with the first cover portion made of rigid or semi-rigid material, so that the operator can grasp the grip portion firmly, and further the remaining portion of the operation section is covered with the second cover portion made of soft material, so that the operation member provided on the operation section can be operated over the second cover portion without difficulty.

BRIEF DESCRIPTION OF THE DRAWINGS

FIG. 1 is a perspective view showing the whole construction of an embodiment of the endoscope system according to the invention;

FIG. 2 is a front view illustrating the construction of the operation section of the endoscope shown in FIG. 1;

FIG. 3 is a perspective view depicting the distal end of the insertion section of the endoscope;

FIG. 4 is a perspective view illustrating the construction of the distal end of the insertion section cover;

FIG. 6 is a cross sectional view depicting the insertion section of the endoscope system according to the invention;

FIG. 7 is a cross sectional view showing the connecting portion of the endoscope system shown in FIG. 7;

FIG. 11 is a perspective view illustrating the end portion of the universal cord of the embodiment shown in FIGS. 9 and 10;

FIGS. 12A and 12B are cross-sectional views showing another embodiment of the protection cover according to the invention;

FIG. 13 is a cross-sectional view illustrating another embodiment of the insertion section cover according to the invention;

FIG. 14 is a schematic view depicting various forceps for use in the endoscope;

FIG. 15 is a graph showing the relation between the outer diameter of the forceps and the number of the forceps;

FIGS. 16 and 17 are schematic views illustrating two embodiments of the endoscope system according to the invention;

FIGS. 18A and 18B depict another embodiment of the endoscope system according to the invention;

FIGS. 19A and 19B show another embodiment of the endoscope system according to the invention;

FIG. 21 is a schematic view showing another embodiment of the protection cover according to the invention;

FIG. 22 is a side view representing the endoscope system using the cover shown in FIG. 21;

FIG. 23 is a perspective view illustrating an embodiment of the grip cover according to the invention;

FIG. 24 is a perspective view showing another embodiment of the grip cover;

FIGS. 27A and 27B depict another embodiment of the endoscope system according to the invention;

FIG. 30 is a cross-sectional view illustrating another embodiment of the protection cover according to the invention;

FIG. 31 is a front view showing the insertion section of the protection cover shown in FIG. 30;

FIGS. 32 and 33 are cross-sectional views cut along lines 32—32 and 33—33 in FIG. 31, respectively;

FIGS. 34A and 34B are cross-sectional views showing the manner of securing the window; and FIGS. 35A, 35B, 35C and 35D are cross-sectional views illustrating several embodiments of the insertion section cover according to the invention.

EXPLANATION OF THE PREFERRED EMBODIMENTS

Figure 5:
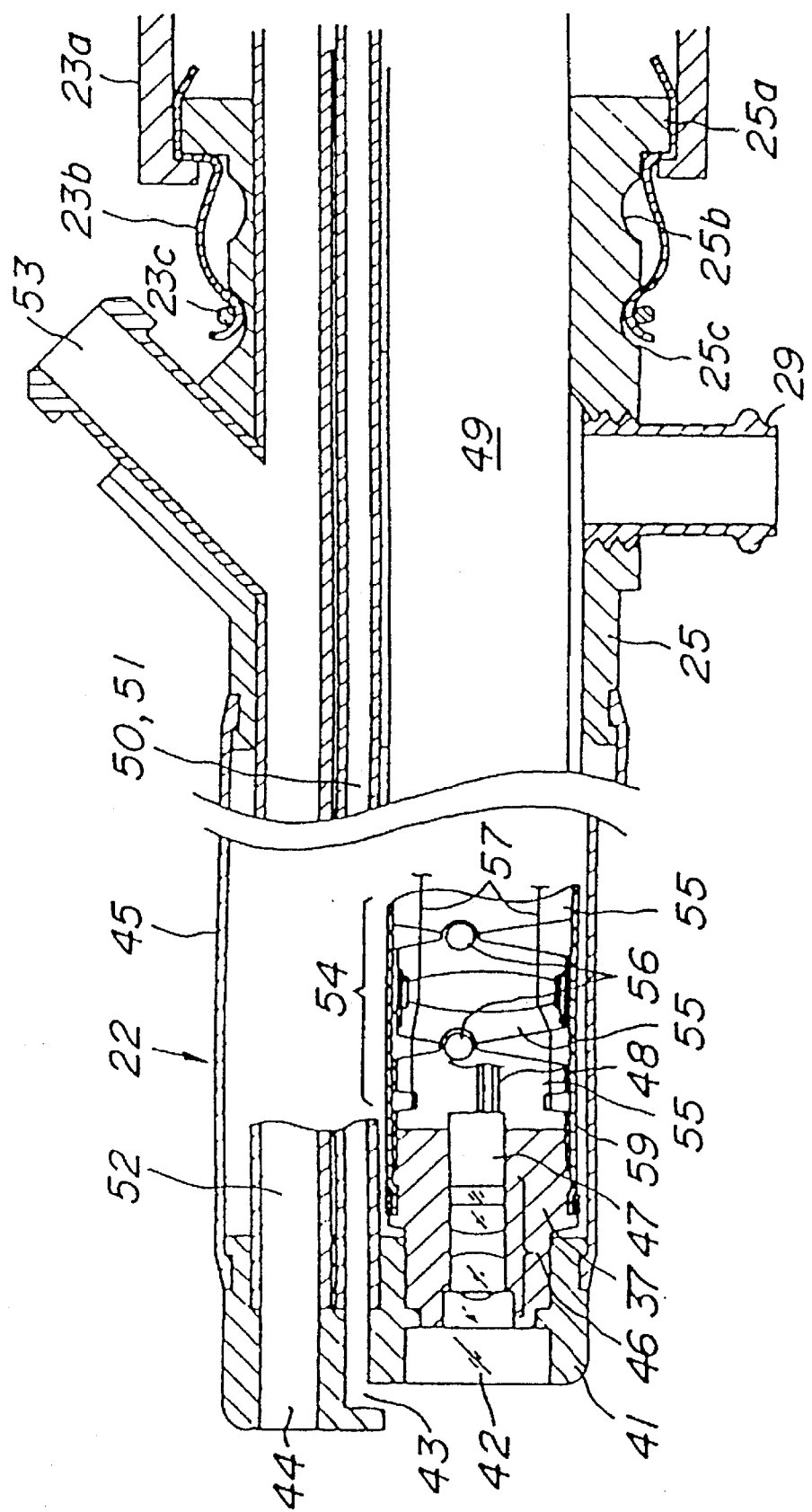
FIG. 5 is a longitudinal cross sectional view showing the endoscope system shown in FIG. 1.

FIG. 1 is a schematic view showing an embodiment of the endoscope system according to the invention including an endoscope apparatus and disposable protection cover. The endoscope apparatus comprises an endoscope 13 having an insertion section 11 and an operation section 12 with which a proximal end of the insertion section is coupled, and an external apparatus 14 coupled with the endoscope 13. The external apparatus 14 comprises a video processor 15 having a circuit for driving a solid state image sensor, provided within a distal end of the insertion section 11, and a circuit for processing an image signal read out of the solid state image sensor, a monitor device 16 for displaying an image of an object under inspection by processing the image signal supplied from the video processor 15, a light source device 17 for emitting light for illuminating the inside of a cavity by means of a light guide optical fiber bundle extending within the insertion section 11, a fluid control device 18 for supplying air and water and sucking liquids, and an inflator 19 for inflating the disposable protection cover in order to inflate the disposable protection cover such that the insertion section 11 of the endoscope 13 can be easily inserted into and removed from the disposable protection cover as will be explained later in detail. These devices are installed in a box 20 having casters. The video processor 15 and light source device 17 are coupled with the operation section 12 of the endoscope 13 by means of signal conductors and a light guide optical fiber bundle provided in a universal cord 21, and the fluid control device 18 is coupled with conduit channels provided within the disposable protection cover by means of conduit tubes arranged along the universal cord 21. The construction and operation of the above-mentioned devices, except for the inflator 19, are well known in the art, so that detailed explanation thereof is dispensed with.

The disposable protection cover of the present embodiment comprises an insertion section cover 22 for covering the insertion section 11 of the endoscope 131, an operation section cover 23 for covering the operation section 12 of the endoscope and a universal cord cover 24 for covering the universal cord 21. These disposable protection covers 22, 23 and 24 are formed separately from each other, and suitable coupling mechanisms are provided between junctions thereof in order to avoid possible contamination through the junctions.

The protection covers 22, 23 and 24 may be made of various materials. For instance, flexible vinyl and rubber may be used as a soft material and rigid or semi-rigid plastics may be used as a hard material. It should be noted that the protection covers 22, 23 and 24 are not always necessarily made of the same material, but may be made of different materials. For instance, the insertion section cover 22 may be made of flexible rubber, the operation section cover 23 may be made of rigid plastics and the universal cord cover 24 may be made of semi-rigid vinyl.

Prior to the actual examination, a set of protection covers is removed from a package and a connecting portion 25 made of rigid or semi-rigid plastics and provided at a proximal end of the insertion section cover 22 is hung from a cover supporting member 27 of a cover supporting device 26. In order to prevent the connecting portion 25 of the insertion section cover 22 from being contaminated, the cover supporting member 27 may be covered with a disposable cover. As will be explained later, the connecting portion 25 of the insertion section cover 22 is utilized to couple the insertion section cover with the operation section cover 23.

The height of the cover supporting member 27 has to be adjusted such that when the insertion section cover 22 is hung from the cover supporting member 27, the distal end of the disposable insertion section cover is not brought into contact with the floor. However, if the height of the cover supporting member 27 is made too high, the inserting operation becomes difficult, so that the cover supporting member should not be made so high. In such a case, the insertion section cover 22 has to be supported by an operator.

After the insertion section cover 22 has been hung from the cover supporting member 27, an end of an air supply tube 28 connected to the inflator 19 is coupled with a nipple portion 29 provided in the connecting portion 25 of the insertion section cover 22, and then the inflator 19 is driven to supply air through the tube 28 into insertion section cover 22. In this manner, the insertion section cover 22 is inflated, so that the insertion section 11 of the endoscope 13 can be easily inserted into the insertion section cover 22. Then, the inflator 19 is de-energized and the tube 28 is decoupled from the nipple portion 29. This inflating operation is also performed upon removing the insertion section 11 from the insertion section cover 22. After the examination, the protection covers 22, 23 and 24 are discarded as medical wastes and the endoscope is cleaned and sterilized after all examinations for one day have been finished.

FIG. 2 shows the construction of the operation section 12 of the endoscope. To the operation section 12 are connected the insertion section 11 and universal cord 21. The operation section 12 comprises a grip portion 31 and a main portion 32. The main portion 32 comprises angle knobs 33 for bending the distal end of the insertion section 11, air and water supply control switch 34, suction control switch 35 and function switch 36 for controlling the operation of a camera taking photographs of the object under inspection. In the present embodiment, the angle knobs 33 are detachably secured to the main portion 32 of the operation section 12. The angle knobs 33 may be of a disposable type which are contained in a package in which the disposable protection cover is installed or may be reusable after sterilization. To the universal cord 21 is connected a connector 21a for connecting a light guide optical fiber bundle 39, conduit tubes and signal conductors to the external apparatus 14.

FIG. 3 is a perspective view illustrating the construction of the insertion section 11 of the endoscope. In the present embodiment, a lateral cross-section of a distal end construction member 37 is semicircular and in a front surface 38 of the member 37 there are arranged outlets of a pair of illuminating optical systems, i.e. optical fiber bundles 39 and an observing optical system 40 provided between the illuminating optical systems.

FIG. 4 is a perspective view depicting the construction of a distal end of the insertion section cover 22 and FIG. 5 is a longitudinal cross-sectional view showing the insertion section cover 22 into which the insertion section 12 of the endoscope is inserted. In a front surface of a distal end construction member 41 of the insertion section cover 22, there are provided a semicircular observation window 42 made of transparent material, a nozzle 43 for ejecting air and water toward the window 42, and an outlet opening 44 of a forceps channel 52. By ejecting the air and water from the nozzle 43, the outer surface of the observation window 42 can be cleaned.

To the distal end construction member 41 of the insertion section cover 22 is connected one end of an insertion section cover tube 45 which isolates a main portion of the insertion section 12 from the outside. This cover tube 45 is made of a flexible material. The other end of the cover tube 45 is connected to the connecting portion 25 of the insertion section cover 22.

As illustrated in FIG. 5, within the distal end construction member 37 of the insertion section 11 which faces with the observation window 42 of the distal end construction member 41 of the insertion section cover 22, there are arranged an observing lens system 46 for forming an image of an object under inspection and a solid state image sensor 47 for picking-up the image of an object under inspection. The solid state image sensor 47 is electrically connected to the video processor 15 (FIG. 1) by means of signal conductors 48 extending through the insertion section 11 and universal cord 21.

Within the insertion section cover 22, there is formed an endoscope insertion channel 49 into which the insertion section 11 is inserted, air supply conduit channel 50 which communicates with the air and water ejecting nozzle 43, water supply conduit channel 51 which also communicates with the nozzle 43, and forceps channel 52. These channels are arranged in parallel with each other. The forceps channel 52 is communicated with a forceps inlet opening 53 provided in the connecting portion 25 and is also communicated with the fluid control device 18 by means of a conduit tube provided within the universal cord 21. Therefore, the forceps channel 52 is sometimes called a suction channel. Further, the conduit channels 50, 51 and forceps channel 52 are also called conduit tubes in the present specification.

In order to bend the distal end of the insertion section 11 by operating the angle knobs 33 such that an optical axis of the observing optical system 46 is moved up and down as well as right and left, there is provided a bending portion 54 adjacent to the distal end construction member 37 of the insertion section 11 of the endoscope. The bending portion 54 comprises a series of nodal rings 55 which are coupled with each other by means of journal pins 56, a front end ring of which is connected to the distal end construction member 37 of the insertion section 11. A pair of wires 57 are secured to the front end ring 55 at diametrically opposing points. These wires 57 are extended within the insertion section 11 and are wound around a pair of pulleys provided in the operation section 12. The series of nodal rings 55 are covered with a flexible rubber tube 59 in a liquid tight manner. By operating the angle knobs 33, the pulleys may be rotated and thus the wires 57, 58 may be moved so as to direct the distal end of the insertion section 11 in a desired direction. This construction is well known in the art, so that its detailed explanation may be dispensed with. At a proximal end of the connecting portion 25, there are formed a ring-shaped recess 25a for connecting the operation section cover 23 and a ring shaped recesses 25b for engaging the connecting portion with the supporting member 27 on the supporting stand 26.

As illustrated in FIG. 5, in the outer surface of the connecting portion 25, there are formed flange 25a and ring shaped recesses 25b and 25c. The operation section cover 23 comprises a first portion 23a made of semi-rigid material and a second portion 23b formed by a flexible tube. An end of the first portion 23a is secured to the flange 25a of the connecting portion 25 while one end of the second portion 23b is clamped between the flange 25a and the first portion 23a. The other end of the second portion 23b is secured to the ring-shaped recess 25c by means of a rubber band 23c. The ring-shaped recess 25b serves to support the insertion section cover 22 onto the supporting member 27 when the insertion section 11 of the endoscope is inserted or removed into or from the insertion section cover 22.

According to the first aspect of the present invention, the forceps channel 52 is constructed such that a plurality of forceps for use in ordinary coverless endoscopes can be commonly utilized. That is to say, the length, inner diameter, strength, material, configuration and shape of the forceps channel of the protection cover are determined such that various types of forceps which have been proposed for coverless endoscopes can be utilized.

FIGS. 6 and 7 show another embodiment of the disposable protection cover for use in the endoscope system according to the present invention. This disposable protection cover is used for an upper endoscope for inspecting and treating the oesophagus, stomach and duodenum. FIG. 6 is a cross-sectional view showing distal end portion 101 and bending portion 102 of an insertion section cover 105 under such a condition that the bending portion is bent at a maximum bending angle so that a radius of curvature R of a longitudinal center axis of a forceps channel tube 103 is at a minimum. In FIGS. 6 and 7, an insertion section 111 of an endoscope inserted into an insertion section inserting channel 104 is shown schematically.

The insertion section cover 105 of the disposable protection cover comprises an outer cover tube 106 and a distal end construction member 107 made of a rigid material. In the distal end construction member 107, an observation window 108 and a forceps outlet opening 109 are formed. A distal end 112 of the insertion section 111 of the endoscope is brought into contact with an inner wall of the observation window 108. The insertion section 111 of the endoscope comprises a bending portion 113. In FIG. 6, the bending portion 113 is bent in an upward direction by a maximum bending angle and to the right by a maximum bending angle. It should be noted that the bending portion 102 and outer cover tube 106 of the insertion section cover 101 are formed such that the bending portion can be bent in accordance with bending movement of the insertion section 111 of the endoscope. In the present embodiment, the maximum upward bending angle of the bending portion 102 of the cover is 210° and the maximum rightward bending angle is 100°, thus a radius of curvature of an inner side of the bending portion 102 is 6 mm.

The distal end construction member 107 has a diameter of 10 mm and has formed therein air and water supply openings. The outer cover tube 106 also has a diameter of 10 mm and is made of resilient synthetic resin having a low sliding friction. The outer cover tube 106 is connected with the distal end construction member 107 in a liquid tight manner. The outer cover tube 106 has a higher flexibility at the bending portion 102 thereof than the remaining portion and has formed therein conduits for inserting the forceps channel tube 103 and the insertion section 111 of the endoscope. The diameter of the forceps channel tube inserting conduit formed within the insertion section cover 105 is slightly larger than the diameter of the forceps channel tube 103. The forceps channel tube 103 is inserted freely into the forceps channel conduit except for both ends thereof.

The forceps channel tube 103 is fabricated using a PTFE tube with a low sliding friction and has an inner diameter of 2.0 mm. A steel wire is wound around the forceps channel tube 103 and a steel wire is wound at the bending portion 102, so that the forceps channel tube is hardly pinched at the bending portion 102 upon bending. The forceps channel tube 103 is communicated with a suction conduit 129 formed in a connecting portion 120, and the suction conduit is connected to a suction device by means of a suction tube 124. In this manner, liquids can be drawn from the distal end of the insertion section cover 105 together with air by means of the forceps channel tube 103. Therefore, the forceps channel tube 103 is sometimes called the suction conduit tube.

In the distal end portion 112 of the insertion section 111 of the endoscope, there are provided an observation lens system, a solid state image sensor and an outlet of the light guide optical fiber bundle. The bending portion 113 of the insertion section 111 of the endoscope has a length of about 100 mm and comprises a series of nodal rings each having a length of 3 to 4 mm. By operating angle knobs provided on the operation section 131 of the endoscope, the bending portion 113 can be bent up and down as well as to the right and left.

The bending portion 113 of the insertion section 111 of the endoscope has an outer tube formed by a synthetic resin tube, such as a silicon rubber tube having a thickness of 0.5 mm. The insertion section 111 of the endoscope comprises a so-called flex formed by a helically wound steel wire tube and a so-called braid formed by winding a fine wire on the flex in a mesh. Around the steel wire tube is provided a synthetic resin tube, such as a urethane tube, having a low slipping friction. The insertion section 111 of the endoscope has an oval cross-section and assumes substantially half of a cross-sectional area of the insertion section cover 101.

As illustrated in FIG. 7, in the connecting portion 120 there is formed a forceps inlet channel 128 having a forceps inlet opening 122. The forceps inlet opening 122 is closed by a forceps plug 121 made of resilient material and having a central slit 121a and a central hole 121b. The forceps inlet channel 128 is communicated with the suction conduit 129 as well as a forceps guide channel 130 which is communicated with the forceps channel tube 103. A diameter of the forceps channel 128 is slightly larger than the diameter of the forceps channel tube 103 or the diameter of the forceps guide conduit 130 and is inclined with respect to a longitudinal axis of the insertion section cover 105 by an angle of 30° to 45°. The diameter of the suction conduit 129 is substantially equal to the diameter of the forceps channel tube 103.

A distal end of the operation section 131 of the endoscope is tapered and is detachably inserted into an operation section inserting opening 132 formed in the connecting portion 120 of the protection cover. At a junction between the insertion section 111 and the operation section 131 of the endoscope, there is formed a step so that a space is formed between the endoscope and the connecting portion 120 of the protection cover, and this space is communicated with the insertion section channel 104. In the connecting portion 120 there is provided a nipple portion 134 which is communicated with the inflator (not shown in FIG. 7) by means of the inflating tube 133.

The connecting portion 120 is made of molded synthetic resin having a low sliding friction such as general-purpose engineering plastics, so that a forceps 147 made of steel or synthetic resin can be smoothly inserted into the forceps inlet channel 128 and forceps guide conduit 130. The proximal end of the forceps channel tube 103 is secured in a liquid tight manner to the forceps guide conduit 130 over a length of about 10 mm by means of an epoxy cementing agent. The outer surface of the forceps channel tube 103 is chemically treated in order to increase the adhesive force. The proximal end of the outer cover tube 106 is fused to the end face of the connecting portion 120 in a water proof fashion as well. A 100 mm portion of the outer cover tube 106 extending from the fused end is formed rather rigidly in order to increase the resiliency of the outer cover tube. Therefore, the outer cover tube 106 is hardly bent at the junction between the connecting portion 120 and the distal end of the outer cover tube.

FIGS. 8A to 8D are schematic views showing the relationship between the disposable protection covers 114 and the forceps 147 which are developed for ordinary coverless endoscopes. The length L1 of the forceps channel defined by the forceps channel tube 103, forceps guide conduit 130 and forceps inlet channel 128 is determined to be shorter than the length L2 of an insertion portion of the forceps 147, i.e. a sum of a length (50 mm) of a distal end portion of the forceps which protrudes from the distal end construction member 107 and a length (150 to 350 mm) of a proximal end portion of the forceps, which is required for operating the forceps, is approximately 200 to 400 mm. The inner diameter of the forceps channel is larger than a maximum outer diameter of a most frequently used forceps by about 0.2 to 0.4 mm. It should be noted that forceps having outer diameters smaller than said maximum outer diameter may be used. The forceps channel should be constructed with a sufficiently large inner diameter and should be made of material having sufficiently large mechanical strength and sufficiently low sliding friction, so that the forceps can be smoothly inserted into the forceps channel using a relatively small force not larger than 1.5 Kg although a length of the distal end construction member 107 of the protection cover is long and the bending portion 102 is bent to the maximum bending angle as shown in FIG. 6.

For instance, the length of the central slit 121a and the length of the diameter of the central hole 121b formed in the forceps plug 121 are larger than the length of the outer diameter of the most frequently used forceps by 1 mm and 0.3 mm, respectively. When this is the case, the forceps can be inserted into the forceps channel without difficulty and the leakage of liquids can be prevented effectively through the use of suction. The slit 121a serves to wipe liquids off the forceps when the forceps is drawn from the forceps channel. When a forceps having a larger diameter is necessary, the forceps plug 121 is removed from the forceps inlet opening 122. To allow repeated removal and insertion, the forceps plug 121 is preferably made of silicon rubber having a tearing strength of 45 Kgf/cm$^2$ under a JIS A-type tear test.

In order to insert and remove the forceps into and out of the forceps channel smoothly, it is preferable that the forceps channel has no sharp steps or bent portions. The inner diameter of the forceps channel is larger than the maximum diameter of the forceps by 0.5 mm and the forceps inlet channel 128 is inclined with respect to the longitudinal axis of the insertion section cover 105 by 32° and the forceps guide conduit 130 is inclined with respect to the longitudinal axis by 10°.

The forceps channel tube 103 is made of a material which has sufficiently high mechanical strength, low sliding friction, large resiliency and is difficult to deform. In the present embodiment, the forceps channel tube 103 is made of non-packed PTFE and has a thickness of 0.5 mm. At the bending portion 102, semicircular recesses having a depth of 0.2 mm are formed in the outer surface at a pitch of 0.5 mm helically. A steel wire having a diameter of 0.2 mm is wound around the bending portion 102 and is fixed to the bending portion 102 by a thin coating of urethane resin. This construction reinforces the bending portion 102 making it difficult for the forceps channel formed therein to become pinched off even when the bending portion 102 is bent to the maximum bending angle such that the radius of curvature R is equal to 7 mm.

In the present embodiment, PTFE has a tensile strength of 300 Kgf/cm$^2$ under ASTM test 638, an expansion ratio of 300% and a durometer hardness of D55 under ASTEM test D2240. The distal end construction member 107 is made of SUS 303 and a portion of the distal end construction member 107 on which the distal end of the forceps channel tube 103 is secured has a length shorter than 5 mm. This allows the forceps channel to be bent smoothly even when the bending portion 102 of the insertion section cover 101 is bent at the maximum bending angle. The forceps channel tube 103 is firmly secured to the distal end construction member 107 in a liquid tight manner by an epoxy resin adhesive agent. The inner diameter of the forceps outlet opening 109 is the same as the inner diameter of the forceps channel tube 103. The inner wall of the forceps outlet opening 109 has a polished surface with a roughness less than 6.3 and a length shorter than 10 mm.

By constructing the disposable protection cover mentioned above, a forceps with a rigid distal end shorter than 15 cm can be smoothly inserted into the forceps channel even under a condition that the bending portion 102 is bent to the maximum bending angle as shown in FIG. 6. It should be noted that the forceps channel tube 103 provided between the distal end construction member 107 and the connecting portion 120 has such a length that the distal end of the tube is able to be deformed and inserted into the forceps outlet opening 109 formed in the distal end construction member 107 by 2 to 3 mm, so that even if the rigid tip of the forceps is brought into contact with the inner wall of the forceps channel tube during the inserting operation, the tube is not extended.

In the present embodiment, in order to utilize a plurality of forceps which have been developed to be used for normal coverless endoscopes and have different lengths, outer diameters and shapes, in accordance with organs to be treated and corresponding treatment, the forceps channels of the disposable protection covers are formed in the following manner.

TABLE 1

| Organs | Forceps | | Forceps Channel | |
|---|---|---|---|---|
| | L 2 mm | Outer diameter mm | L 1 mm | Inner diameter mm |
| Stomach | Biopsy Forceps 1550 | 2.6 | 1030 | 2.8 |
| | Grasping Forceps 1650 | 3.3 | 1030 | 3.7 |
| Duodenum | Diathernary Wire Cutter 1900 | 1.8 | 1300 | 2.0 |
| | Diathernary Coagulator 1900 | 1.8 | 1300 | 2.0 |
| Ileum | Grasping Forceps 1650 | 3.4 | 1350 | 3.7 |

Figure 8A:
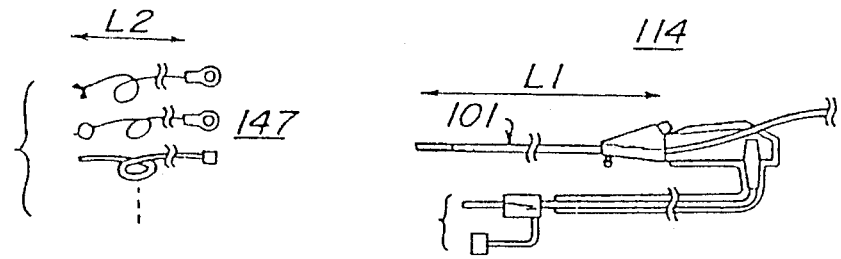
FIGS. 8A, 8B, 8C and 8D are schematic views illustrating the overall construction of the endoscope system according to the invention.
Figure 8B:
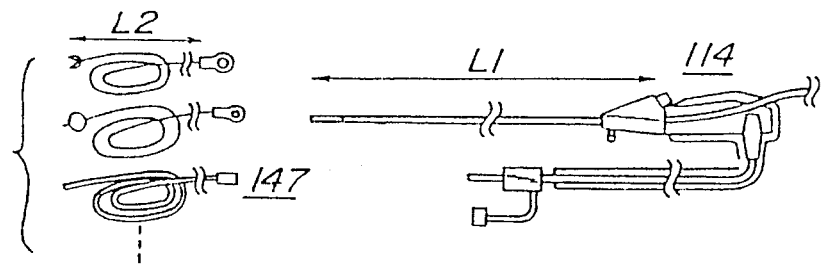
Figure 8C:
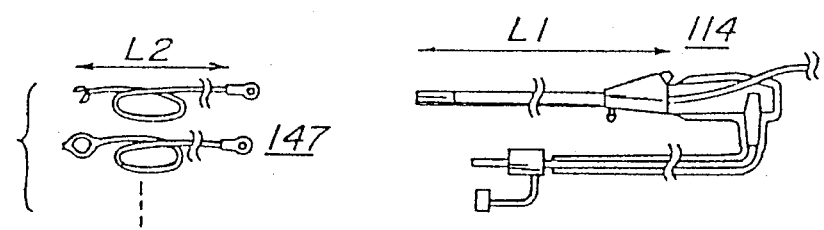

When it is desired to use an upper forceps 147 having the length L2 of 1550 to 1650 mm and an outer diameter of 2.4 to 2.6 mm as shown in FIG. 8A for the oesophagus, stomach and duodenum, a disposable protection cover comprising the forceps channel having a length L1 of 1330 mm and a inner diameter of 2.8 mm may be employed. Further, when it is desired to use an upper forceps 147 having a length L2 of 1650 mm and an outer diameter of 3.3 to 3.5 mm as shown in FIG. 8B for the ileum, a disposable protection cover comprising the forceps channel having a length L1 of 1350 mm and an inner diameter of 3.7 mm may be employed.

Figure 8D:
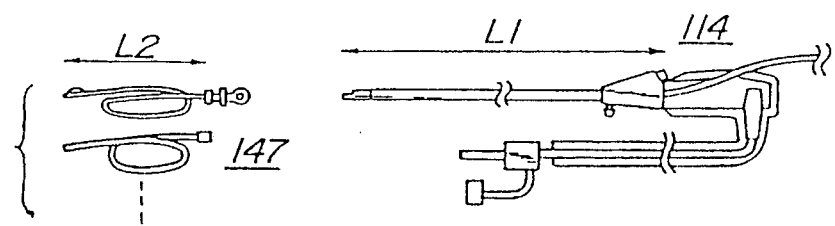

When it is required to employ forceps having a length L2 of 1550 to 1650 mm and an outer diameter of 3.3 mm as illustrated in FIG. 3C for the stomach, a disposable protection cover comprising the forceps channel having a length L1 of 1350 mm and an inner diameter of 3.7 mm may be used. Moreover, when it is desired to use forceps having a length L2 of 1800 to 2000 mm and an outer diameter of 1.8 mm for the duodenum as shown in FIG. 8D, a disposable protection cover with the forceps channel having a length L1 of 1300 mm and an inner diameter of 2.0 mm may be employed.

In order to distinguish the forceps and disposable protection covers easily, forceps and covers belonging to the same group may be colored the same. Further, the forceps channel may be provided such that when the disposable protection cover is bent, the forceps channel becomes an inner side. Moreover, it is not always necessary to form the bending portion 102 of the disposable protection cover such that the bending portion is bent circularly, but it may be constructed such that the curvature of the bending portion is gradually smaller toward the distal end construction member 107 so that the forceps can be easily inserted. Further, the forceps channel tube 103 may be reinforced at a junction point between the connecting portion 120 or may be reinforced by providing the steel wire over its whole length.

It should be further noted that the endoscope may be of the fiber scope type or may have a plurality of forceps channels. Moreover, the combination of the forceps and disposable protection covers is not limited to the above-explained combination, but may be modified in various ways. For instance, disposable protection covers may be constructed to be used together with forceps which have been developed for urinary organs, respiratory organs, obstetrics and gynecology and so on.

As explained above, according to the present embodiment, the operator can employ a number of forceps which have been developed for ordinary coverless endoscopes also in the endoscope system including the disposable protection cover. Therefore, it is no longer necessary to prepare a new set of forceps which have been or will be developed to be exclusively used for the endoscope system. Moreover, when the forceps are used in the endoscope system including the disposable protection cover, the forceps can be easily prepared and erroneous usage of the forceps can be prevented. Further, the operator can use the usually used forceps, so that the treatment can be carried out effectively. It should be noted that the coverless endoscope or the with-cover endoscope can be selectively used in accordance with the infection of patients, and thus the endoscope system can be constructed in an economical and efficient manner.

Figure 9:
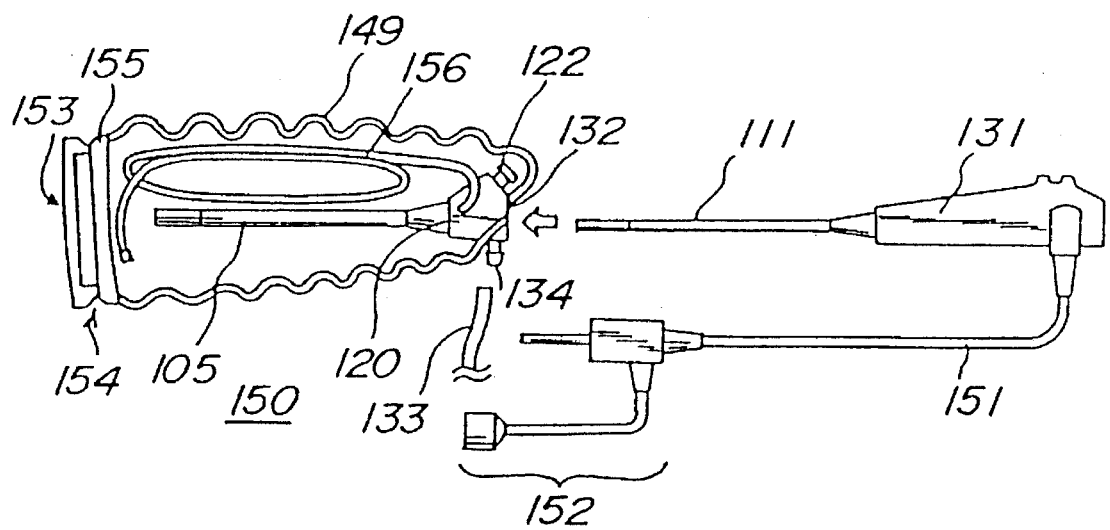
FIGS. 9 and 10 are schematic side views showing another embodiment of the endoscope system according to the invention.
Figure 10:
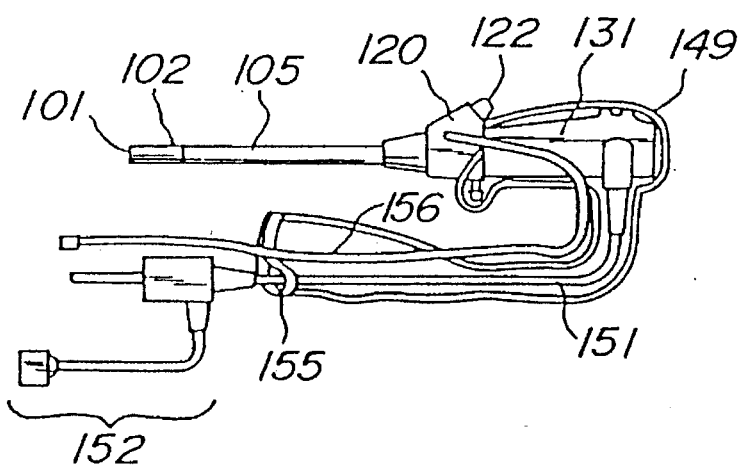

FIGS. 9 to 11 show several embodiments of the disposable protection cover for use in the endoscope system according to the invention. The disposable protection cover comprises an insertion section cover having a connecting portion into which the operation section of the endoscope is inserted, an outer cover for surrounding the insertion section cover, one end of the outer cover being secured to a distal end of the connecting portion and the other end having formed therein an opening and the outer cover being made of resilient material, a means for closing the opening of the outer cover in such a manner that said opening can be easily opened, and a means for keeping the opened opening of the outer cover such that the endoscope can be easily inserted into the outer cover through the opening and for fixing the opening to the endoscope.

In FIG. 9, the disposable protection cover 150 comprises an insertion section cover 105, a connecting portion 120 connected to the insertion section cover at its proximal end and having a forceps inlet opening 122 and an inflating tube nipple portion 134, an air and water supply tube member 156 and an outer cover 149 which surrounds all the above-mentioned parts as illustrated in FIG. 9. The outer cover 149 is formed in the shape of a tube having a large diameter and one end of the outer cover is secured to the connecting portion 120 in a liquid tight manner. The outer cover 149 is made of a transparent synthetic resin sheet having a thickness smaller than 0.5 mm and having good waterproof and expansion properties. For instance, the outer cover 149 may be made of inexpensive PVC.

At the other end of the outer cover 149, there is provided an opening formed by a band member 155 which is constructed by a resilient synthetic resin having a thin metal wire embedded therein. The opening is closed by a sealing member 153 made of a synthetic resin sheet such as a PS sheet having a thickness smaller than 0.2 mm, so that the sealing member 153 can be easily broken. To this end, a cut-in portion 154 is formed in the sealing member 153. After exhausting the inside of the outer cover 149, the sealing member 153 is fused to the band member 155, and then the whole assembly is sterilized by radiation.

Upon using the above-mentioned disposable protection cover 150, the cover is first taken out of a package and an inflating tube 133 is connected to the nipple portion 134 to inflate the insertion section cover 105. Then, the insertion section 111 of the endoscope is inserted into the insertion section cover 105, and further the operation section 131 is inserted into the tapered inlet opening 132 of the connecting portion 120.

Next, the sealing member 153 is broken along the cut-in portion 154 and then the closed band member 155 is deformed into a substantially circular configuration. Then, the band member 155 is moved relative to the parts 105, 120, 156 surrounded by the outer cover 149 to expose these parts. At the same time, the operation section 131 and universal cord 151 are covered with the outer cover 149 as shown in FIG. 10. It should be noted that the outer cover 149 is preformed such that a portion which surrounds the operation section 131 has a large diameter and a portion covering the universal cord 151 has a small diameter.

After that, the band member 155 is deformed to surround the universal cord 151 such that the tube member 156 is also surrounded by the band member as illustrated in FIG. 11. Then, the universal cord 151 is coupled with the light source device as well as the video processor by means of a connector 152, and further the tube member 156 is coupled with the fluid control device.

After the examination, the band member 155 is manually widened by use of the hands and the outer cover 149 is removed to expose the tube member 156, universal cord 151 and the operation section 131 of the endoscope. Then, the outer cover 149 is turned over to surround the connecting portion 120, insertion section cover 105 and tube member 156, and the band member 155 is deformed again to close the opening of the outer cover 149.

In the disposable protection cover 150 shown in FIGS. 9 to 11, the sterilizing pack and the outer cover 149 are formed integrally as a unitary body, so that the cost can be decreased and further the preparation can be carried out within a short time. Moreover, the disposable protection covers of the present embodiment can be stacked one on the other, so that necessary space for storing the covers can be reduced. Furthermore, the opening of the outer cover 149 is formed by the band member 155 having a metal wire embedded therein, and thus the opening can be easily deformed in a desired shape and the covering operation can be performed easily and efficiently. For instance, the band member 155 can be firmly secured to the universal cord 151; the band member is rarely loosened or removed from the universal cord during the examination.

Further, after the examination, the contaminated surface of the insertion section cover 105 is covered with the outer cover 149 such that its clean surface faces outward, so that the operator can be effectively protected from the contamination. Since the one end of the outer cover 149 is secured to the connecting portion 120 in a liquid tight manner, the endoscope is not contaminated. The relative position of the outer cover 149 and the connecting portion 120 is fixed; the outer cover can be preformed in accordance with the outer configuration of the endoscope.

In the embodiments so far explained, upon inserting the insertion section of the endoscope into the insertion section cover, the insertion section inserting channel is inflated. However, when the insertion section is inserted into the insertion section inserting channel 104, air flows out of the cover from the inlet opening 132. Therefore, the output pressure of the inflator has to be increased or a sealing means has to be provided on the insertion section of the endoscope. However, when the sealing means is provided, the inserting operation might be difficult, particularly for a long insertion section. In order to inflate easily the insertion section inserting channel 104, a thickness of the construction member defining the insertion section inserting channel 104 may be thin. However, in such a case, the mechanical strength becomes weak, and the protection cover might be broken during the inserting operation.

FIGS. 12A and 12B show another embodiment of the disposable protection cover according to the invention, in which the insertion section of the endoscope can be easily inserted into the cover. FIG. 12B is a cross-sectional view cut along a line 128—128 in FIG. 12A. In the present embodiment, the disposable protection cover comprises an inflating conduit channel near the insertion section inserting channel such that a thin deformable partition is formed between the insertion section inserting channel and the inflating conduit channel, an inflating conduit formed in the connecting portion communicates with the inflating conduit channel, and a nipple portion provided in the connecting portion communicates with the inflating conduit. To the nipple portion an inflating tube is connectable.

In FIGS. 12A and 12B, portions similar to the previous embodiment are denoted by the same reference numerals, and explanation thereof is dispensed with. In the present embodiment, the insertion section cover 105 is constructed to have air and water supply conduits 60 and insertion section inserting channel 104 integral as a unitary body. Between the insertion section inserting channel 104 and the forceps channel tube 103 there is formed an inflating conduit channel 158 which extends along the whole length of the insertion section inserting channel 104. The inflating conduit channel 158 has a slit-like cross-sectional configuration. A size of the insertion section inserting channel 104 is made identical with or slightly smaller than that of the insertion section of the endoscope.

The insertion section cover 105 is formed as a multilumen tube having a plurality of holes formed therein and is secured to the connecting portion 120 in a liquid tight manner. The connecting portion 120 is formed by a mold of synthetic resin such as elastomer which is sufficiently resilient and soft and also can be reused. A plurality of holes and nipple portions are simultaneously formed during the molding.

Between the insertion section inserting channel 104 and the inflating conduit channel 158 there is formed a partition 159 having a very thin thickness smaller than 0.5 mm, so that the partition is easily deformed. The nipple portion 134 is coupled with an inflator 157 by means of the inflating tube 133. It should be noted that in the present embodiment, the inflator 157 is formed by a suction pump for sucking air within the inflating conduit channel 158 to inflate the insertion section inserting channel 104. This sucking operation may be carried out by means of a syringe or by the operator. In this case, after the insertion section channel 104 is expanded, the inflating tube 133 is pinched off by means of a suitable clip. In this manner, the partition 159 is deformed such that the insertion section inserting channel 104 is expanded, so that the insertion section can be easily inserted into the channel.

After the insertion section of the endoscope has been fully inserted into the insertion section inserting channel 104, air is introduced into the inflating conduit channel 158 and the partition 159 recovers its original shape and the insertion section of the endoscope can be firmly fixed within the insertion section cover 105. Upon removing the insertion section of the endoscope from the disposable protection cover, the air is sucked from the inflating conduit channel 158.

In the present embodiment, it is not necessary to form a space between the inner wall of the insertion section inserting channel 104 and the outer surface of the insertion section of the endoscope, and further the inflating conduit channel 158 can be formed in a dead space. Therefore, the diameter of the insertion section cover 105 can be small. Furthermore, the partition 159 can be deformed easily, so that the output power of the inflator 157 may be small. Therefore, the inflator 157 can be cheap and power can be saved.

Moreover, by sucking the air from the inflating conduit channel 158, the partition 159 is displaced toward the forceps channel tube 103, so that the insertion section inserting channel 104 is expanded. Therefore, the insertion section of the endoscope can be easily inserted into and removed from the channel 104, so that it is no longer necessary to prepare a large size cover supporting device. Further, during the examination, the inflating conduit channel 158 serves as an air cushion for the forceps channel tube 103 and the necessary force for inserting the insertion section into the cover can be reduced depending upon the bending angle.

FIG. 13 is a cross-sectional view showing an alternative of the embodiment illustrated in FIGS. 12A and 12B. In the present embodiment, two inflating conduit channels 158 are provided on both sides of the forceps channel tube 103. Therefore, a cross-sectional area of the insertion section inserting channel 104 is larger than that of the previous embodiment without reducing a thickness of the partition 159. Upon inserting the insertion section of the endoscope into the insertion section inserting channel 104, the inflating conduit channels 158 are communicated with the atmosphere, and after that, these channels are inflated to fix the insertion section in a desired position. The construction of the present embodiment is particularly advantageous for a protection cover having an insertion section cover with a relatively large diameter.

In the embodiment shown in FIG. 13, the operation for inserting and removing the insertion section of the endoscope can be performed easily, and further during the examination, the channels 158 are inflated, so that they can give a resiliency. It should be noted that in the embodiments shown in FIGS. 12 and 13, the partition 159 may be provided separately from the cover tube.

Figure 14:
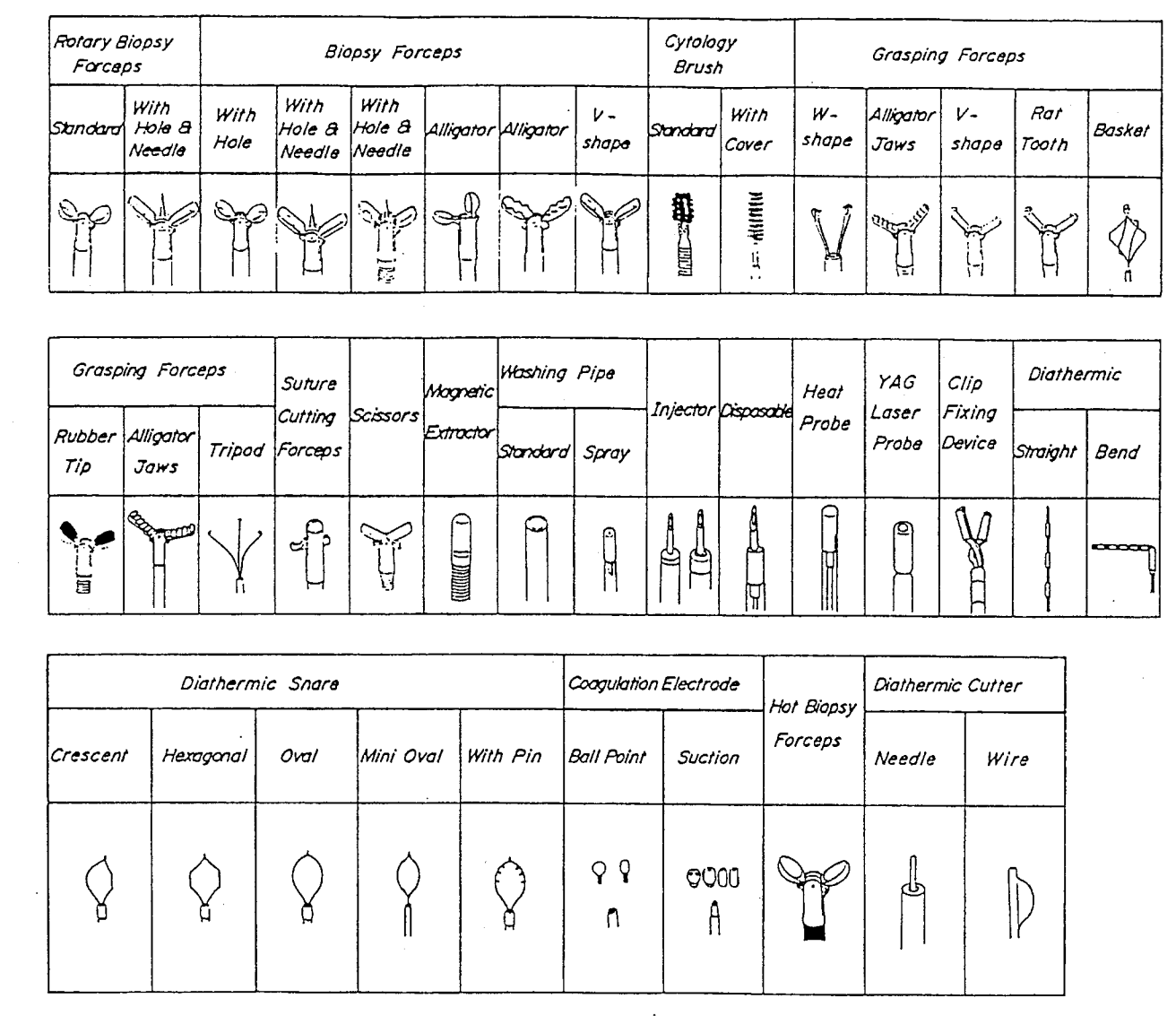

FIG. 14 shows various types forceps for use in upper endoscopes. It should be noted that several of the same type of forceps having different outer diameters are prepared. FIG. 15 is a histogram representing the number of forceps having different outer diameters and the following Table 2 shows the relationship between the number of forceps and the outer diameters. When the existing forceps are classified in accordance with the outer diameter, there are several peaks in the number of the forceps, as depicted in FIG. 15. In the present specification, a forceps whose outer diameter corresponds to a peak is called a standard forceps or most frequently used forceps. In FIG. 15, there are three standard forceps having the outer-diameters of 1.8 mm, 2.4 mm and 3.1 mm. According to the invention, there are prepared a plurality of disposable protection covers including forceps channels having inner diameters which are larger than outer diameters of the standard forceps by 1.1 to 1.4 times.

TABLE 2

| Diameter of existing forceps (mm) | The number forceps | Amount of Sales | Inner diameter of forceps channel |
|---|---|---|---|
| 1.0 | 2 | small | |
| 1.2 | 2 | small | |
| 1.3 | 3 | medium | |
| 1.6 | 1 | small | |
| 1.7 | 1 | very small | |
| 1.8 | 6 | large | 2.0 (mm) |
| 1.9 | 2 | small | |
| 2.0 | 1 | very small | |
| 2.3 | 2 | small | |
| 2.4 | 8 | large | 2.8 (mm) |
| 2.5 | 1 | very small | |
| 2.6 | 1 | very small | |
| 3.0 | 2 | small | |
| 3.1 | 10 | large | 3.7 (mm) |
| 3.2 | 5 | small | |

According to the present invention, a lower limit of the inner diameter of the forceps channel is determined to be larger than the outer diameter of the standard forceps by 1.1 times. This is due to the fact that a forceps having a large outer diameter can be used even if the forceps channel is bent or the forceps has a long distal end construction member, because the treatment can be performed efficiently by using the forceps having a large outer diameter. An upper limit of the inner diameter of the forceps channel is determined to be larger than the outer diameter of the standard forceps by 1.4 times. This is due to the fact that even a forceps having a particularly long distal end construction member can be inserted, the suction through the forceps channel can be maintained when the forceps is inserted into the forceps channel, and an outer diameter of the insertion section of the protection cover should not be made large.

Judging from the histogram shown in FIG. 15 and Table 2, the inner diameter series of the forceps channels are determined such that the most frequently used forceps can be also utilized in the endoscope system including the disposable protection cover. In the present embodiment, there are prepared three types of disposable protection covers with forceps channels having inner diameters of 2.0 mm, 2.8 mm and 3.7 mm for forceps having outer diameters 1.8 mm, 2.4 mm and 3.1 mm, respectively.

FIG. 16 illustrates the whole construction of the endoscope system according to the invention. On a right hand side there are shown protection covers 114 for videoscopes and on a left side there are depicted protection covers 114 for fiberscopes. An inner diameter of the forceps channels of disposable protection covers depicted in the uppermost column is 2.0 mm, and thus the forceps 147 having outer diameters smaller than 1.8 mm can be utilized for these protection covers. The disposable protection covers shown in a second column have forceps channels having inner diameters of also 2.0 mm, but have the forceps channels longer than the above-mentioned covers, so that forceps having outer diameters smaller than 1.8 mm and having longer lengths can be employed for these covers. The protection covers shown in a third column have forceps channels having an inner diameter of 2.8 mm, and therefore the forceps having outer diameters smaller than 2.4 mm can be used. The inner diameter of the forceps channels of the protection covers in a fourth column is 3.7 mm, and the forceps having outer-diameters smaller than 3.1 can be utilized.

The above-mentioned inner diameter series of the forceps channels is an example, and the inner diameters of the forceps channels may be 2.2 mm, 3.2 mm and 4.2 mm for outer diameters of the forceps of 1.8 mm, 2.4 mm and 3.1 mm, respectively by considering the length of the distal end construction members of the forceps and the sucking efficiency. Further, the above-mentioned inner diameter series is for the forceps for treating the stomach, so that for forceps for treating other organs, other inner diameter series may be prepared.

Furthermore, the inner diameter series of the forceps channels of the disposable protection covers may be determined in accordance with the inner diameter series of the forceps channel of the existing coverless endoscopes. That is to say, inner diameters of the forceps channels of the protection covers may be identical with inner diameters of the forceps channels of a plurality of the most frequently used coverless endoscopes.

Table 3 represents the inner diameter series of the forceps channels of the existing coverless endoscopes. In the endoscope system according to the invention, an endoscope can be commonly used for a plurality of disposable protection covers with forceps channels having different inner diameters. In the present embodiment, a desired cover may be selected from three kinds of covers including the forceps channels having inner diameters of 2.0 mm, 2.8 and 3.7 mm or 2.2 mm, 3.2 mm and 4.2 mm. Therefore, it is no longer necessary to prepare forty one different kinds of protection covers with forceps channels having inner diameters from 1 mm to 5 mm, each being different from one another by 0.5 mm, and it is sufficient to prepare the three kinds of protection covers with the forceps channels having different inner diameters. In Table 3, the coverless upper endoscopes having forceps channels of 1.5 mm, 2.0 mm, 2.8 mm and 3.7 mm are most frequently used, so that in the present embodiment there are prepared four different kinds of disposable protection covers with forceps channels of 1.5 mm, 2.0 mm, 2.8 mm and 3.7 mm.

TABLE 3

| Inner diameter of forceps channel of without-cover endoscope (mm) | Inner diameter of forceps channel in cover (mm) |
|---|---|
| 1.2 | |
| 1.5 | 1.5 |
| 1.7 | |
| 2.0 | 2.0 |
| 2.2 | |
| 2.6 | |
| 2.8 | 2.8 |
| 3.2 | |
| 3.7 | 3.7 |
| 4.2 | |

FIG. 17 illustrates a whole construction of the endoscope system according to the invention. On a left side there are shown coverless endoscopes 136 and on a right side there are shown videoscopes with protection covers. An inner diameter of the forceps channels of the coverless endoscopes 136 and disposable protection covers 114 depicted in the uppermost column is 1.5 mm and thus the forceps 147 having the outer diameters of 1.0 to 1.3 mm can be utilized. The coverless endoscopes and disposable protection covers shown in a second column have forceps channels having an inner diameter of 2.0 so that the forceps having outer diameters of 1.6 to 1.8 mm can be employed. The coverless endoscopes and protection covers shown in a third column have forceps channels having an inner diameter of 2.8 mm, and therefore forceps having outer diameters of 1.9 to 2.4 mm can be used. The inner diameter of the forceps channels of the protection covers in a fourth column is 3.7 mm, and forceps having outer diameters of 2.5 to 3.3 mm can be utilized.

The above-mentioned example is for the inner diameter series of forceps channels of the disposable protection cover for the upper endoscope for stomach, and different inner diameter series may be adopted for various organs other than the stomach.

FIGS. 18A and 18B show another embodiment of the disposable protection cover according to the invention. A protection cover 150 of the present embodiment is similar to the embodiment illustrated in FIGS. 9 to 11, but differs in a point that a grip cover 161 is provided between the connecting portion 120 and the outer cover 149. The connecting portion 120 is made of rigid or semi-rigid synthetic resin, and the outer cover 149 is formed by a thin synthetic resin sheet. If the grip portion of the operation section 131 of the endoscope is covered with the outer cover 149, the outer cover might slip on the grip portion. In the present embodiment, the grip cover 161 is made of soft and elastic material such as synthetic rubber and elastomer. Further the grip cover 161 is formed to be tightly smaller than the grip portion so that the grip cover can be tightly fixed on the grip portion.

The grip cover 161 is fused to the connecting portion 120 as well as to the outer cover 149 in a liquid tight manner and has formed therein a cut-out portion 164 so that the movable portions of the operation section 131, such as the operation buttons 163 and angle knobs (not shown) and a projection 162 at the connection to the universal cord 151, are not covered with the grip cover. At the front end of the outer cover 149 there is provided a band member 155 defining the opening.

The disposable protection cover 150 of the present embodiment can be used in entirely the same manner as the embodiment illustrated in FIGS. 9 to 11. In this case, the grip portion of the operation section 131 of the endoscope is covered with the grip cover 161 made of elastic material, and thus the operator can grasp the grip portion firmly over the grip cover.

It should be noted that the cut-out portion 164 formed in the grip cover 161 may be closed by a very thin film or a plurality of holes formed in the grip cover through which the operation buttons protrude from the grip cover. Moreover, anti-slip ridges may be formed on an outer surface of the grip cover at portions to be grasped by the operator's fingers.

FIGS. 19A and 19B depict another embodiment of the endoscope system according to the invention. In the present embodiment, the proximal and of the connecting portion 120 is extended to form an extended portion, and the outer cover 149 is secured to an edge of the extended portion. The extended portion of the connecting portion 120 has a thickness smaller than that of the remaining portion of the connecting portion 120, and a plurality of operation buttons 163 are provided in the extended portion of the connecting portion 120. The configuration of the extended portion of the connecting portion 120 is made substantially identical with the outer configuration of the operation section 131 of the endoscope. Also in the present embodiment, the outer cover 149 has formed therein the cut-out portion 164 so that the angle knobs 168 are exposed. Since the cut-out portion 164 is rather large, the operator can easily operate the angle knobs 168 without difficulty.

When the operator grips the grip portion of the operation section 131 of the endoscope, two electric operation switches (tact switches) 163 for driving electromagnetic valves which control the air supply, water supply and suction are operated by an index finger of the operator and two electric operation switches (tact switches) 163 for controlling the video processor, e.g. freeze switch and release switch, are operated by a thumb of the operator. The operation switches 163 are covered with resilient material, and conductors connected to the switches extend through a tube 156 to an electric connector (not shown). Within the tube 156 there are also arranged air and water supply tube member 161 and suction tube 124 to form the universal cord.

As shown in FIG. 19B, the signal conductors 119 connected to the solid state image sensor, arranged within the distal end of the insertion section 111, are extended through the operation section 131 as well as through the universal cord 151. The universal cord 151 extends from the operation section 131 at its proximal end. The endoscope can be easily inserted into the protection cover without being affected by the universal cord 151. When the operation section 131 and universal cord 151 are covered with the outer cover 149, the operation buttons 163 are exposed, so that the operator can easily and positively operate these buttons.

Figures 20A, 20B:
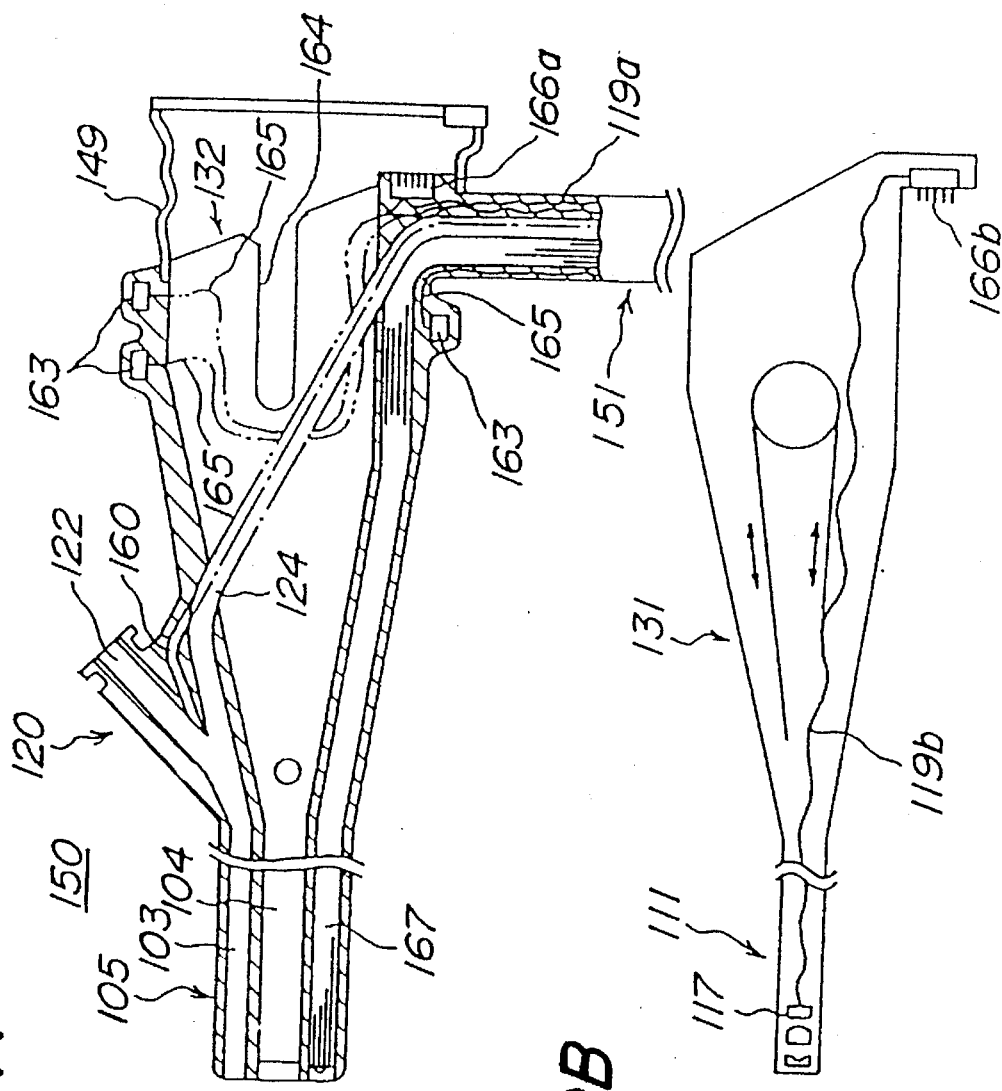
FIGS. 20A and 20B illustrate another embodiment of the endoscope system according to the invention.

FIGS. 20A and 20B show another embodiment of the endoscope system according to the invention. In the present embodiment, a light guide optical fiber bundle is provided in the disposable protection cover. That is to say, a light guide optical fiber bundle 167 is extended within the insertion section cover 105 in parallel with the insertion section inserting channel 104 and forceps channel 103. The light guide optical fiber bundle 167 is passed through the connecting portion 120 and is extended out of the connecting portion as the universal cord 151. The air and water supply tube member 160 and suction tube 124 are also extended out of the connecting portion 120 together with the light guide optical fiber bundle 167. The conductors 165 connected to the operation switches 163 are extended within the extended portion of the connecting portion 120 and are connected to the connector (not shown) by means of the universal cord 151. A connector 166*a* is secured to the proximal end of the extended portion of the connecting portion 120. The opening of the outer cover 149 is closed by the chucking means 153.

The signal conductors 119*b* connected to the solid state image sensor 117 provided in the distal end of the insertion section 111 are connected to a socket 166*b* secured to the operation section 131 of the endoscope. When the endoscope is inserted into the protection cover, the socket 166*b* is electrically and mechanically coupled with the connector 166*a*. In this manner the solid state image sensor 117 is connected to the video processor.

The extended portion of the connecting portion 120 of the cover is formed integrally with the connecting portion by molding. When forming the connecting portion 120, first a base member having a large thickness is formed, then various parts are fixed on the base member and finally a thin synthetic resin film is coated. In order to couple the parts with the base member smoothly without producing steps, recesses and depressions are previously formed in the outer surface of the base member. It should be noted that the extended portion of the connecting portion 120 has to be formed such that the grip portion can be firmly grasped and the operation buttons can be positively operated without being affected by the extended portion.

In the present embodiment, the air and water supply tube member 160, suction tube 124, light guide optical fiber bundle 167, conductors 165 and signal conductors 119*a* all are provided in the universal cord 151, so that the operation of covering the endoscope with the protection cover and the operation of handling the endoscope during examination can be performed easily and positively.

In the embodiments shown in FIGS. 18 to 20, the angle knobs may be detachably secured to the shaft provided on the operation section. In such a case, a relatively small aperture may be formed in the extended portion of the connecting portion, and thus the cut-out portion may be smaller.

According to one aspect of the present invention, the operation section cover of the disposable protection cover comprises a grip cover for covering the grip portion of the operation section and being made of rigid or semi-rigid material and a top cover for covering the remaining portion of the operation section and being made of soft material, so that the operator can grasp the grip portion firmly, FIG. 21 shows such a disposable protection cover according to the invention. A disposable protection cover 250 of the present embodiment comprises, in addition to the insertion section inserting channel, a forceps channel and an air and water supply channel. That is to say, the protection cover 250 comprises a rigid distal end construction member 201, flexible insertion section cover 215, connecting portion 220, air and water supply tube member 256, outer cover 249, forceps plug 221, inflating tube 233 and three kinds of grip covers 275 having different materials, sizes and shapes.

The distal end construction member 201, insertion section cover 215 and connecting portion 220 are coupled with each other in a liquid tight manner. In the connecting portion 220, forceps inlet opening 226 and nipple portion 234 for connecting the inflating tube and operation section inserting opening 232 are formed. One end of the outer cover 249 is secured to the connecting portion 220 along the periphery of the opening 232 and nipple portion 234. The outer cover 249 is made of a transparent synthetic resin sheet such as PVC having a thickness smaller than 0.5 mm. The outer cover 249 can be expanded and covers the operation section 231 of the endoscope and universal cord 251 up to its connector as illustrated in FIG. 22. In a shrunken state of the outer cover 249, the outer cover surrounds the insertion section cover 215 and connecting portion 220 as shown in FIG. 21. The outer cover 249 has an opening formed at its other end by a band member 255 which is constructed by a resilient synthetic resin having a thin metal wire embedded therein. The opening is closed by a sealing member 253 made of a synthetic resin sheet such as a PS sheet having a thickness smaller than 0.2 mm, so that the sealing member 253 can be easily broken. To this end, a cut-in portion 254 is formed in the sealing member 253. After exhausting (evacuating) the inside of the outer cover 249, the sealing member 253 is fused to the band member 255, and then the whole assembly is sterilized by radiation. It should be noted that a free end of the tube member 256 is closed by a sealing member.

In the present embodiment, within the outer cover 249, the forceps plug 221, inflating tube 233 and three kinds of grip portions 275 are arranged. At first, the sealing member 253 is removed and the above-mentioned parts are removed from the outer cover. The manner of using the disposable protection cover of the present embodiment is similar to that which has been explained before with reference to the embodiment illustrated in FIGS. 9 to 11, but in the present embodiment, after the operation portion of the endoscope is covered with the outer cover 249, the grip portion of the endoscope is further covered with the rigid or semi-rigid grip cover 275, so that the operator can grasp the grip portion of the endoscope firmly. Moreover, the operator can select the most suitable grip cover 275 from the three kinds of grip covers.

FIG. 23 shows an embodiment of the grip cover 275. The grip cover 257 comprises snap-fits 278 which utilize the resiliency of the synthetic material such as polyethylene, polypropylene, urethane rubber and elastomer, so that the grip cover can be easily and positively coupled with the proximal end of the connecting portion 220. The grip cover 275 further comprises a hinge portion 277 along which a half body of the grip cover can be bent. The half body of the grip cover 275 is opened as shown by a chain line in FIG. 23, and the base body is secured to the connecting portion 220 by means of the snap-fit 278. Then, the half body is coupled with the base body by means of the snap-fit 278.

FIG. 24 illustrates another embodiment of the grip cover 275 according to the invention. The grip cover has a substantially U-shaped cross-section and is coupled with the connecting portion 220 having a corresponding snap-fit 278 by inserting the ridge-like snap-fit 278 of the grip cover 275 into the groove-like snap-fit 278 of the connecting portion 220. Further, in the present embodiment, on an outer surface of the grip cover 275 there are formed non-slip V-shaped ridges 276. In the embodiment shown in FIG. 23, non-slip projections 276 are formed on the grip cover 275 such that the projections are aligned in a V-shape on the side walls and are distributed on the front surface. In this manner, the operator can grasp the grip portion of the endoscope firmly.

Figure 25:
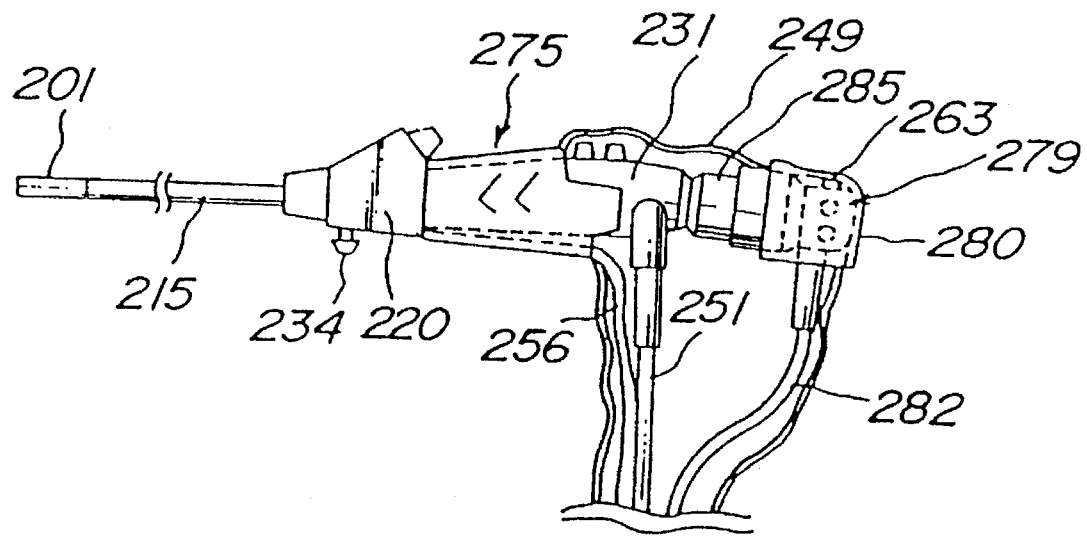
FIG. 25 is a schematic side view showing another embodiment of the endoscope system according to the invention.

FIG. 25 illustrates another embodiment of the endoscope system according to the invention. In the present embodiment, use is made of a fiberscope, and a video camera 279 is arranged at an eyepiece portion 285. A video signal generated by the video camera 279 is supplied via a video cable 282 to the video processor. The video camera 279 and video cable 282 are also covered with the outer cover 249 together with the universal cord 251.

Figure 26:
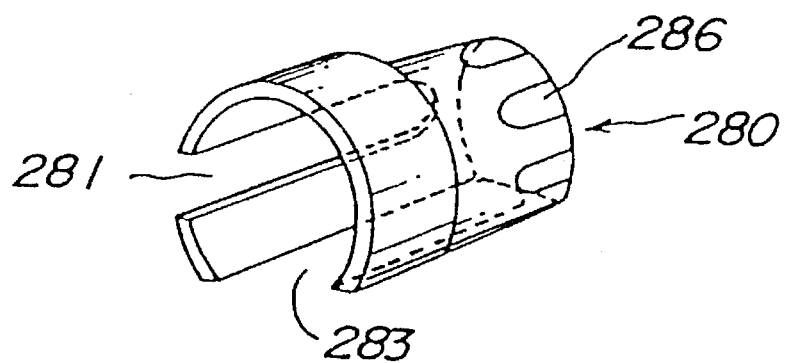
FIG. 26 is a perspective view illustrating the video camera cap shown in FIG. 25.

After the video camera 279 is provided on the eyepiece portion 285, they are surrounded by the outer cover 249. In this case, if the universal cord 251 and video cable 282 have different lengths, the shorter one is extruded from the outer cover 249. When the operation buttons 263 of the video camera 280 are covered with the outer cover 249, these buttons can not be operated easily. In the present embodiment, in order to overcome such a disadvantage, a cap 280 shown in FIG. 26 is secured to the head of the video camera 279. The cap 280 is formed to correspond to the outer configuration of the head of the video camera and is made of relatively soft transparent material, such as natural rubber, synthetic rubber and elastomer. Thin portions 286 are formed at positions corresponding to the operation buttons 263 of the video camera 279. Further cut-out portions 281 and 283 are formed in the cap 280 at positions corresponding to a zooming knob and connector to the video cable 282. The cap 280 is installed within the outer cover 249 together with the grip cover 275.

After the operation section 231 of the endoscope is covered with the outer cover 249, the cap 280 is set on the head of the video camera 279, so that the outer cover is closely applied on the camera head. In this case, the operation buttons 263 of the video camera 279 can be easily operated by means of the thin portions 286 and the zooming knob can be operated also easily. It should be noted that the cap 280 may be formed by two separate bodies or two half bodies may be coupled along the hinge.

FIGS. 27A and 27B depict another embodiment of the endoscope system according to the invention. In the present embodiment, the video camera 279 and video cable 282 are covered with a second outer cover 249a which is formed separately from the outer cover 249. In the outer cover 249, there is formed a sealing end 253a at a position corresponding to the eyepiece portion 285 and a rubber band 284 for securing the sealing end 253a at the eyepiece portion as illustrated by chain lines.

As shown in FIG. 27B, at one end of the second outer cover 249a, there is provided a rubber band 284a for securing the cover to the camera head in a liquid tight manner. At the other end of the second outer cover 249a there is provided a band member 255a which can be deformed into a desired shape. The second outer cover 249a is installed within the outer cover 249, in a folded condition, as shown by chain lines in FIG. 27A.

In the present embodiment, when the video camera 279 is not coupled with the eyepiece portion 285, the eyepiece portion is covered with the outer cover 249 and is secured to the eyepiece portion by means of the rubber band 284 in a liquid tight manner and the image of the object can be observed by means of the eyepiece in the usual manner. Further, when the video camera 279 is coupled with the eyepiece portion 285, the second outer cover 249a can be secured to the head portion of the eyepiece portion by means of the rubber tube 284a in a liquid tight manner. In this case the second outer cover 249a can be easily secured to the eyepiece portion. Further, the band member 255a and rubber band 284a can be easily deformed into desired shapes, so that various types of video cameras can be utilized.

In the above embodiments, the insertion section cover 205 and outer cover 249 are formed integrally as a unitary body, but they may be separated from each other. Further, the grip cover 275 may be directly applied on the grip portion of the operation section of the endoscope. In such a case, the junction between the grip cover and the operation section cover has to be overlapped or connected with each other such that the endoscope is not exposed.

Figure 28A:
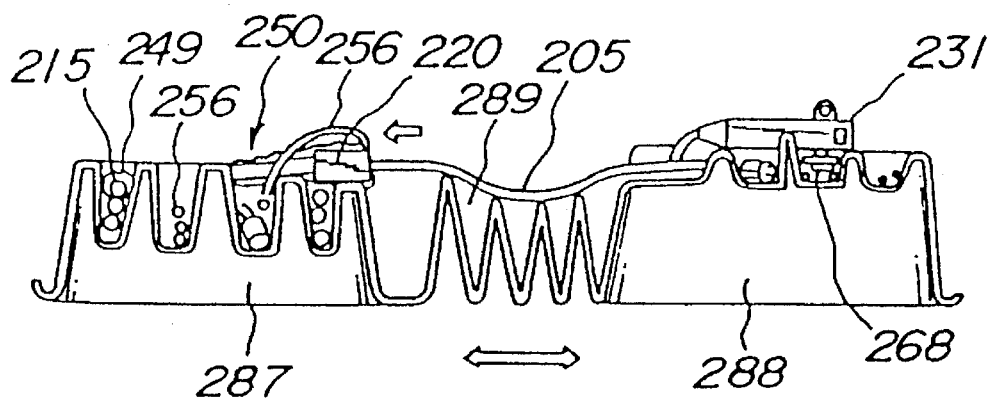
FIGS. 28A and 28B show an embodiment of the apparatus for inserting the endoscope into the protection cover according to the invention.
Figure 28B:
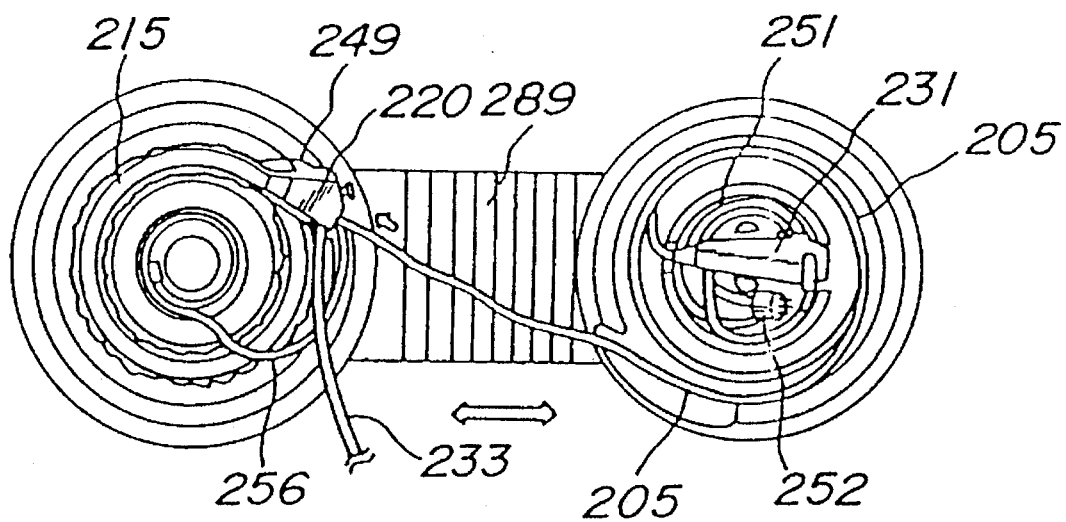

FIGS. 28A and 28B show an embodiment of an apparatus which is effectively used upon inserting the endoscope 211 into the disposable protection cover 250. This apparatus comprises first tray 287 for supporting the cover 250, second tray 288 for holding the endoscope 211 and bellows portion 289 for coupling the first and second trays in such a manner that a distance between these trays can be adjusted. The first and second trays 287, 288 and 289 are formed in an economical manner by plastic molding which is cheap and reusable. In upper surfaces of the first and second trays 287 and 288, inner and outer circular grooves are formed coaxially.

In the inner groove of the first tray 287, the tube member 256 and its connector are inserted, and in the outer groove the insertion section cover 205 is inserted. The tube members 256 and insertion section cover 205 are wound in the counter-clockwise direction. The insertion section cover 205 has to be wound loosely to have a large radius of curvature so that the insertion section of the endoscope can be easily inserted into the insertion section cover. The connecting portion 220 and a substantially half portion of the insertion section cover are covered with the outer cover 249. The connecting portion 220 is indexed at a recess formed in a top of the outermost ridge in the first tray 287 so that the connecting portion can be coupled with the inflator by means of the inflating tube 233.

The universal cord 251 and its connector are installed in the outer groove of the second tray 288, and insertion section 205 of the endoscope is placed in the inner groove. The universal cord 251 and insertion section 205 are wound in the clockwise direction. A cut-out portion is formed in the outer groove, and the insertion section 205 is extended therefrom. In a central depression of the second tray 288, the operation section 231 is inserted such that the angle knobs 268 are faced downward.

The insertion section 205 of the endoscope is supported by the bellows portion 289 and there is formed a space between the side wall of the first tray 287 and the left side wall of the bellows portion such that the index finger and thumb of the operator can be inserted therein. In FIG. 28A, a height of the bellows portion 289 is lower than the upper surfaces of the trays 287 and 288 so that the insertion section 205 is slightly bent downward. However, when the first and second trays 287 and 288 are moved closer to each other, the height of the bellows portion 289 is increased, and when these trays are moved away from each other, the height of the bellows portion decreases. Therefore, the distance between the first and second trays 287 and 288 is adjusted such that a height of the bellows portion become substantially equal to a height of the trays.

When the insertion section 205 is inserted into the cover, first the inserting section is picked-up by the operator in his/her right hand and the distal end portion of the insertion section is inserted into the connecting portion 220 slightly. Then, the insertion section 205 is picked-up by the operator in his/her left hand and the second tray 288 is moved toward the first tray 287 to insert the insertion section into the cover. It should be noted that the insertion section cover is inflated. Next, the insertion section 205 is pulled out of the second tray 288 and is placed on the bellows portion 289 while the second tray is moved away from the first tray 287. Then, the above mentioned operation is repeated. In this manner, the insertion section 205 can be inserted into the insertion section cover 215 in an easy and positive manner without using a large stand for supporting the insertion section cover.

It should be noted that in the above embodiment, the first and second trays 287 and 288 are formed integrally with each other, together with the bellows portion 289. However, the first tray may be formed separately from the first tray. Then, the first tray may be utilized as a part of the package for the disposable protection cover, and the second tray may be used for storing the endoscope.

Figure 29A:
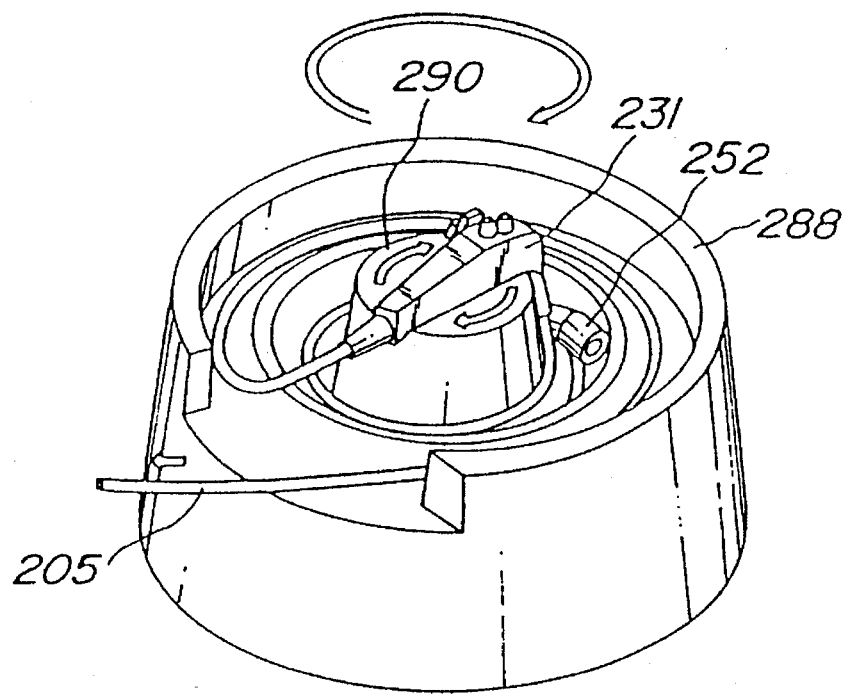
FIGS. 29A and 29B represent still another embodiment of the apparatus according to the invention.
Figure 29B:
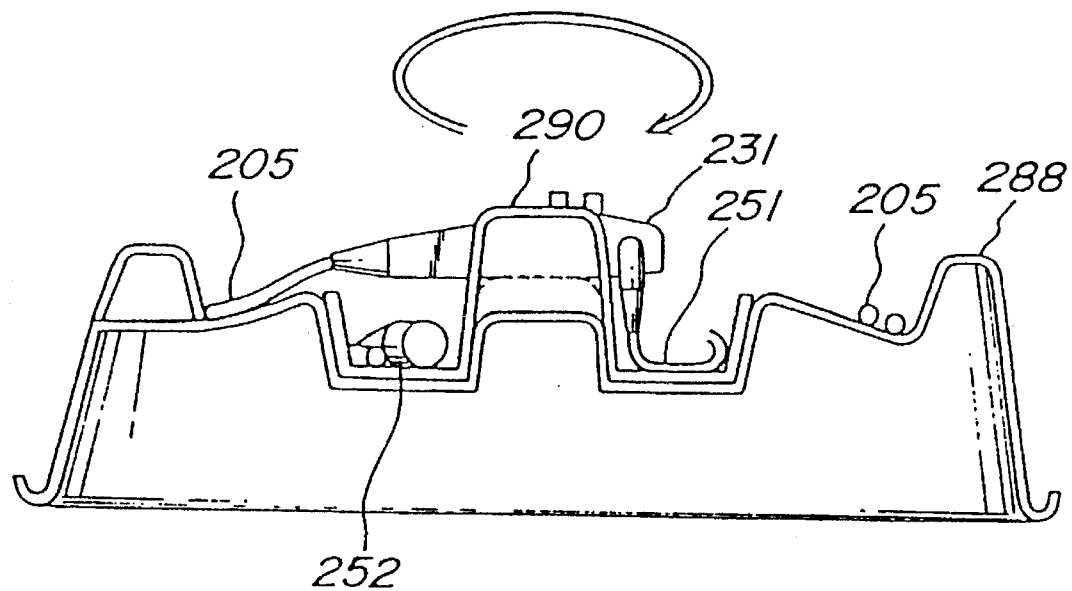

FIGS. 29A and 29B illustrate another embodiment of the second tray 288 of the inserting apparatus according to the invention. In the present embodiment, in the second tray 288 there is provided rotatably a center tray 290 having the inner groove formed therein, and the operation section 231 is placed on the center tray such that the shaft to which the angle knobs are detachably secured faces upward. The outer groove is inclined outward such that the insertion section 205 is moved outward by the force of gravity. The universal cord 251 and its connector are installed in the inner groove.

In the present embodiment, when the center tray 290 is rotated, the insertion section 205 is automatically extruded from the outer groove, so that the inserting operation is much easier and further the insertion section is not picked-up by the operator, and thus it is hardly damaged. It should be noted that the second tray 288 may be arranged to be rotated by 90 degrees such that the insertion section 205 is wound around a horizontal axis. Then, the insertion section may be inserted into the insertion section cover which is hung by means of a suitable stand.

FIG. 30 is a schematic view showing another embodiment of the present invention. In this embodiment, a disposable protection cover 450 comprises a distal end portion 401, an insertion section cover 415 and a connecting portion 420. In the distal end portion 401, a distal end construction member 407 is arranged. In a tip portion of the distal end construction member 407, a window 408 for observation and lighting, a forceps outlet opening 409 and a washing nozzle 469 for the window 408 are arranged as illustrated in FIG. 31 showing a front view from a tip portion side. In a rear portion of the distal end construction member 407, an insertion section inserting tube 470 defining an insertion section inserting channel 404, a forceps channel tube 471 defining a forceps channel 403 and an air and water supply tube 460 defining an air and water channel are respectively connected to the window 408, the forceps outlet opening 409 and washing nozzle 469, as illustrated in FIG. 32, which is a cross-sectional view taken along line 32—32 of FIG. 30.

In the insertion section cover 415, an outer cover tube 406 is connected in a liquid tight manner between the distal end construction member 407 of the distal end portion 401 and the connecting portion 420. In the outer cover tube 406, the insertion section inserting tube 470, the forceps channel tube 471 and the air and water supply tube 460 are arranged in an extended manner. The outer cover tube 406 needs good flexibility characteristics, waterproof properties, slidability, safety, and so on. Therefore, the outer cover tube 406 is formed by, for example, a tube member such that synthetic resins are coated on a member stacking a steel flex and a steel braid. Moreover, since the outer cover tube 406 needs flexibility, twistability, elasticity and bendability for easy insertion into an internal organ under a condition such that an endoscope (not shown) is inserted, it is necessary to choose materials, thickness of outer cover tube 406, and a construction of the outer cover tube 406 so that the outer cover tube 406 has elasticity at a bending portion near the distal end portion. It should be noted that the bending portion of the outer cover tube 406 may be constructed by an another cover member such as a thin member made of a synthetic rubber tube.

In the connecting portion 420, connector portions of the insertion section inserting tube 470, the forceps channel tube 471 and the air and water supply tube 460 are arranged in a tip side thereof, and tubes corresponding to these members are connected to the connector portions in a liquid tight manner.

In this embodiment, respective tubes 460, 470, 471 and the outer cover tube 406 are connected in a straight manner by, for example, inserting a hard rod, and in such a manner that respective tubes are not rotated by using a mark etc, so that a center axis 0 of the forceps channel tube 471 illustrated in FIG. 33, which is a cross-sectional taken along line 33—33 of FIG. 30, is identical with a center axis 0 of the forceps channel tube 471 illustrated in FIG. 32, which is a cross-sectional view taken along line 32—32 of FIG. 30, under such a condition that the insertion section cover 415 is extended naturally. Therefore, if the insertion section cover 415 is extended naturally, the center axes 0 of the forceps channel tube 471 are always identical at arbitrary cross-sections in the insertion section cover 415. In this case, respective tubes 460, 470 and 471 are made of synthetic resins, such as PTFE having good flexibility and slidability characteristics, and have a bending strength and a tensile strength sufficient to endure a bending force generated when the bending force is applied to the tube 470 having an endoscope set therein.

Moreover, in the connecting portion 420, a forceps guide conduit 428, having a forceps inlet opening 422 for inserting a forceps 447 and communicating with the forceps channel 403, is arranged in an inclined manner, and an operation section inlet opening 432 having a cone shape and communicating with the insertion section inserting channel 404 is also arranged. In the forceps guide conduit 428, a forceps plug connecting portion 426 is formed integrally to the forceps inlet opening 422, so that a forceps plug 421 can be detachably arranged. Moreover, two branch portions are arranged in the forceps guide conduit 428 between the forceps inlet opening 428 and the forceps channel tube. A suction conduit 429 and a nipple portion 425 are arranged integrally with the branch portion of the distal end side, and a water supply conduit 474 and a nipple portion 472 are arranged integrally with the branch portion of the proximal end side. A proximal end side suction tube 424 is connected to the nipple portion 425, and a water supply tube 473 for supplying a physiological saline solution is connected to the nipple portion 472.

Further, in the connecting portion 420, an inflating conduit 435 communicating with the operation section inlet opening 432 and the insertion section inserting tube 404, and a nipple portion 434 of an inflating tube are integrally arranged. Therefore, in the case of an endoscope inserting operation, it is possible to inflate the insertion section inserting tube 470 so as to insert easily the endoscope, if an inflating tube (not shown) is connected to the nipple portion 434 and air is supplied.

As mentioned above, according to this embodiment, the center axes 0 of the forceps channel tube 471 are identical at arbitrary cross-sections in the insertion section cover 415 under a condition such that the insertion section cover 415 is naturally extended. Therefore, center positions of the forceps channel tube 471 do not vary greatly between cross-sections spaced a distance smaller than a length of the rigid distal end portion of the forceps 447 in the insertion section cover 415, if the forceps channel tube 471 is bent or twisted due to the bending or twisting of the insertion section cover 415 with a large curvature along for example the esophagus, intestines, etc. or due to the bending or twisting of the bending portion with a small curvature in the up and down or right and left directions.

Therefore, if the forceps 447 is inserted from the forceps inlet opening 422 through the forceps guide conduit 428 and the forceps channel 403, and a tip portion of the forceps 447 is projected from the forceps outlet opening 409 to perform the operation, it is possible to insert the forceps 447 without making contact with the forceps channel tube 471, and thus it is possible to reduce the insertion force. Moreover, since the forceps 471 can be inserted smoothly, it is possible to use forceps 447 having an outer diameter with a relatively large size substantially equal to an inner diameter of the forceps channel 403, and forceps 447 having a long rigid distal end portion can be used.

Moreover, in this embodiment the suction conduit 429 and the nipple portion 425 for the proximal end side suction tube, and the water supply conduit 474 and the nipple portion 472 are arranged in the forceps guide conduit 428 integrally with the connecting portion. Therefore, if it is necessary to keep a field of view clear by supplying continuously a physiological saline solution such as when performing endoscope observation in the gall or urinary organs among the internal organs, it is possible to keep the field of view clear by supplying the physiological saline solution from the nipple portion 472, stopping the supply of the physiological saline solution and sucking out the physiological saline solution via the nipple portion 425. Further, it is possible to wash an inner surface of the organs by supplying a large amount of the physiological saline solution from the nipple portion 472, and to color an inner surface of the organs by supplying coloring solutions from the nipple portion 472.

In this manner, since the water supply conduit 474 is arranged in the forceps guide conduit 428 separately from the suction conduit 429, it is possible to keep the field of view clear by only using the disposable protection cover 450, and thus it is not necessary to prepare other tubes, such as T-shaped tubes. Moreover, since the water supply conduit 474 and the nipple portion 472 are arranged integrally with the connecting portion 420, the total cost can be reduced. Further, since the water supply conduit 474 and the water supply tube 473 can be sterilized at the same time with the disposable protection cover 450, it is very convenient to use. After use, since it is possible to dispose the water supply conduit 474 and the water supply tube 473 at the same time as well as the disposable protection cover 450, it is possible to eliminate washing and sterilizing operations.

In the construction shown in FIG. 30, various methods can be applied for arranging the window 408 for the observation and lighting in the distal and construction member 407. For example, the window 408 may be adhered to the distal end construction member 407 by using adhesive agents, adhesive agents of ultra-violet hardening type, rapidly-drying type adhesive agents, and so on. Moreover, the distal end construction member 407 and the window 408 may be integrally formed by using transparent materials, and then portions other than the window 408 may be shielded by paint. However, in the case of using adhesive agents, it is not easy to automate the assembling operation, and the assembling operation takes a lot of time due to a drying operation of the adhesive agents. In the case of using the adhesive agents of ultra-violet hardening type, it is difficult to control an amount of the adhesive agent to be used. In the case of using the rapidly drying adhesive agents, it is not easy to handle the adhesive agents, and the window 408 may become opaque. Further, in the case of shielding the portions other than the window 408, the total cost of assembly becomes large. Especially, in the disposable protection cover 450, since it is disposed of after using one time, it is necessary to manufacture a large number of the disposable protection covers 450 rapidly and inexpensively, as compared with conventional endoscopes without covers. Therefore, the assembling operation is desired to be automated.

In the embodiment mentioned above, the window 408 is fused by using an ultrasonic wave and connected to the distal end construction member 407. The ultrasonic wave fusing operation is performed by arranging a projection 407a, contacting with a whole bottom circular portion of the window 408, in the distal end construction member 407 as shown in FIG. 34A, or by arranging a step portion 407b, contacting with a whole edge portion of the window 408, in the distal end construction member 407 as shown in FIG. 34B. In this case, the window 408 is formed by transparent synthetic resins such as polycarbonate, polystyrene and so on, which are suitable for the ultrasonic wave fusing operation, and the distal end construction member 407 is formed by the same materials as that of the window 408 or other materials such as modified polyphenylene oxide, preferably colored black.

In this manner, after the distal end construction member 407 is secured by a supporting member and the window 408 is set in the connecting portion of the distal end construction member 407, an ultrasonic wave horn is brought into contact with the window 408 so as to transmit an ultrasonic oscillation to the window 408. In the embodiment shown in FIG. 34A, the projection 407a is fused by friction heat concentrated on the projection 407a, and in the embodiment shown in FIG. 34B, the edge portion of the window 400 is fused by a sheering force. In both cases, the fused portion assumes a liquid tight state. As mentioned above, if the window 408 is connected to the distal end construction member 407 by using ultrasonic wave fusing, the assembling operation becomes easily automated, and thus it is possible to manufacture the disposable protection covers 450 rapidly in a large scale.

The present invention is not limited to the embodiments mentioned above, but various modifications are possible. For example, in the embodiment mentioned above, the air and water supply tube 460 is also arranged at the same positions at the cross-sections between a portion near the distal end portion 401 and a portion near the connecting portion 420 and the insertion section cover 415 as shown in FIGS. 31 and 32, but it is possible to vary the positions of the portions at the cross-sections corresponding to a layout of the distal end construction member 407 or a layout of the connecting portion 420, since only fluid is passing through the air and water supply tube 460. Moreover, the insertion section inserting channel 404 is arranged preferably at the same positions on the cross-sections mentioned above, but it is possible to vary the positions thereof slightly.

Further, in the embodiment mentioned above, the water supply conduit 474 is arranged to the forceps guide conduit 428, but the other water supply conduit 474 could be further formed along the distal end portion 401, the insertion section 415 and the connecting portion 420 in addition to the forceps guide conduit 428. Moreover, in the embodiment mentioned above, the forceps plug 421 is connected to the forceps plug connecting portion 426, but it is possible to use a so-called T-shaped tube instead of the forceps plug 421. Further, the nipple portion 425 for the proximal end side suction tube and the nipple portion 472 are arranged at an upper surface of the connecting portion 420, but they can be arranged at a side surface or at a rear portion thereof if it does not disturb operation of the forceps 447.

Further, in the embodiment mentioned above, the outer cover tube 406, the air and water supply tube 460, the insertion section inserting tube 470 and the forceps channel tube 471 are formed respectively by different tube members, but it is possible to form all or a part of them integrally to construct a multilumen. FIGS. 35A to 35D are cross-sectional views respectively showing the multilumen construction. In FIG. 35A, the insertion section inserting channel 404 and the outer cover tube 406 are formed integrally, and an air supply tube 460a, a water supply tube 460b and the forceps channel tube 471 are formed independently. In FIG. 35B, the forceps channel 403 and the outer cover tube 406 are formed integrally, and the air supply tube 460a, the water supply tube 460b and the insertion section inserting channel 470 are formed independently.

Moreover, in FIG. 35C, the forceps channel 403, the air supply tube 460a, the water supply tube 460b and the outer cover tube 406 are formed integrally, and the insertion section inserting tube 470 is formed independently. In FIG. 35D, all the channels are formed integrally with the outer cover tube 406. In FIGS. 34A to 34D it is possible to construct the air supply tube 460a and the water supply tube 460b as one channel. Further, various multilumen constructions can also be used.

What is claimed is:

1. A protection cover for use in an endoscope system including an endoscope having an insertion section insertable into a cavity under inspection and an operation section to which a proximal end of the insertion section is connected and a protection cover having an insertion section cover for covering said insertion section of the endoscope and an operation section cover for covering said operation section of the endoscope, the improvement being characterized in that said operation section cover comprises a first cover portion for covering a grip portion of said operation section and made of rigid or semi-rigid material and a second cover portion for covering the remaining portion of the operation section of the endoscope and made of soft material.

2. A protection cover according to claim 1, wherein said cover is disposable.

3. In a protection cover for use in an endoscope system including an endoscope having an insertion section insertable into a cavity under inspection and an operation section to which a proximal end of the insertion section is connected and a protection cover for covering said endoscope, the improvement being characterized in that said protection cover comprises an insertion section cover for covering said insertion section of the endoscope, a connection portion having a first end connected to a proximal end of said insertion section cover and for covering a grip portion of the operation section of the endoscope, an outer cover having a first end connected to a second end of the connecting portion and an opening formed in a second end of said outer cover, a means for closing said opening of the outer cover in such a manner that said opening can be opened, and a means for (i) maintaining said opening of the outer cover in an opened condition such that the endoscope can be easily inserted into the outer cover through said opening and (ii) fixing an outer periphery of the opening to the endoscope, wherein (i) said insertion section cover and connecting portion are surrounded by said outer cover and (ii) said opening of the outer cover is closed before usage.

4. A protection cover according to claim 3, wherein said means for maintaining said opening of the outer cover in the opened condition comprises a resilient member having a metal wire embedded therein.

5. In a protection cover for use in an endoscope system including an endoscope having an insertion section insertable into a cavity under inspection and an operation section having at least one operation switch, said operation section being connected to a proximal end of said insertion section, said protection cover having an insertion section cover for covering said insertion section of the endoscope and an operation section cover for covering and surrounding said operation section of the endoscope, the improvement being characterized in that said operation section cover is constructed to cover said operation section of the endoscope in an airtight manner and includes at least one switch provided in an outer surface of the operation section cover.

6. A protection cover for covering an endoscope, the endoscope having an insertion section and an operation section connected to one end of the insertion section, said cover comprising:

an insertion section cover for covering the insertion section of the endoscope; and an operation section cover for covering the operation section of the endoscope and comprising (i) a first cover portion, for covering a first portion of the operation section of the endoscope, formed of a material having a first rigidity value, and (ii) a second cover portion, for covering a second portion of the operation section of the endoscope, formed of a material having a second rigidity value, said second rigidity value being less than said first rigidity value.

7. A cover according to claim 6, wherein said cover is disposable.

8. A protection cover for use in an endoscope system including an endoscope having an insertion section insertable into a cavity under inspection and an operation section having a grip portion and at least one electric switch, said operation section being connected to a proximal end of said insertion section, said protection cover having an insertion section cover for covering said insertion section of the endoscope and an operation section cover for covering said operation section of the endoscope, said operation section cover comprising a grip cover made of elastomer so as to be capable of tightly covering said grip portion of the operation section of the endoscope and said electric switch being exposed outside the protection cover so as to be accessible by a user outside said protection cover.

9. A protection cover for use in covering an endoscope having an insertion section insertable into a cavity to be inspected and a operation section connected to a proximal end of the insertion section, said cover comprising:

an insertion section cover for receiving therein the insertion section of the endoscope; and an operation section cover for receiving therein and surrounding the operation section of the endoscope and comprising at least one switch, for performing a predetermined operation, which can be selectively operated by an operator.

10. In a protection cover for use in an endoscope system including an endoscope having an insertion section insertable into a cavity under inspection and an operation section to which a proximal end of the insertion section is connected, said protection cover being for covering said endoscope, the improvement being characterized in that said protection cover comprises an insertion section cover for covering said insertion section of the endoscope, an operation section cover for covering said operation section of the endoscope and being made of soft material, and a grip portion cover for covering a grip portion of the operation section and being made of hard or semi-hard material.

11. A protection cover according to claim 10, wherein said operation section cover made of soft material is coupled with said insertion section cover to form a single integral body.

12. A protection cover according to claim 10, wherein said grip portion cover made of hard or semi-hard material comprises one of a plurality of grip portion covers having different shapes from each other.

* * * * *